(12) United States Patent
Chiba et al.

(10) Patent No.: US 8,439,851 B2
(45) Date of Patent: May 14, 2013

(54) LUMEN PASSABILITY CHECKING DEVICE, LUMEN PASSABILITY CHECKING METHOD, AND METHOD OF MANUFACTURING LUMEN PASSABILITY CHECKING DEVICE

(75) Inventors: Atsushi Chiba, Hachioji (JP); Takeshi Yokoi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 843 days.

(21) Appl. No.: 12/544,775

(22) Filed: Aug. 20, 2009

(65) Prior Publication Data

US 2009/0312787 A1 Dec. 17, 2009

Related U.S. Application Data

(63) Continuation of application No. PCT/JP2008/053678, filed on Feb. 29, 2008.

(30) Foreign Application Priority Data

Mar. 1, 2007 (JP) .................................. 2007-051969

(51) Int. Cl.
*A61M 29/00* (2006.01)
(52) U.S. Cl.
USPC ........................................................ 600/593
(58) Field of Classification Search .................. 600/593, 600/587
See application file for complete search history.

(56) References Cited

U.S. PATENT DOCUMENTS

| | | | |
|---|---|---|---|
| 3,450,254 A * | 6/1969 | Miles | 206/216 |
| 6,733,512 B2 * | 5/2004 | McGhan | 606/192 |
| 6,950,690 B1 | 9/2005 | Meron et al. | |
| 7,083,578 B2 * | 8/2006 | Lewkowicz et al. | 600/593 |
| 7,083,579 B2 * | 8/2006 | Yokoi et al. | 600/593 |
| 7,585,283 B2 * | 9/2009 | Kraizer et al. | 600/593 |
| 7,749,254 B2 * | 7/2010 | Sobelman et al. | 606/256 |
| 2002/0022829 A1 * | 2/2002 | Nagase et al. | 606/12 |
| 2003/0040685 A1 | 2/2003 | Lewkowicz et al. | |

(Continued)

FOREIGN PATENT DOCUMENTS

| | | |
|---|---|---|
| JP | 2003-524448 | 8/2003 |
| JP | 2003-325438 A | 11/2003 |

(Continued)

OTHER PUBLICATIONS

European Search Report dated Dec. 21, 2011 from corresponding European Patent Application No. EP 08 72 1098.5.

(Continued)

*Primary Examiner* — Sean P Dougherty
*Assistant Examiner* — Michael C Stout
(74) *Attorney, Agent, or Firm* — Scully, Scott, Murphy & Presser, P.C.

(57) ABSTRACT

A lumen passability checking device includes: an expandable and shrinkable outer casing that contains a predetermined fluid, is expanded by a pressure of the contained fluid, and forms an external diameter substantially equal to that of a capsule medical device to be inserted into a body of a subject; and a shape manipulating unit that flows out the fluid contained in the outer casing to shrink-deform the outer casing. The outer casing is shrink-deformed by flowing out the fluid, while maintaining a state of being integrated with the shape manipulating unit.

5 Claims, 15 Drawing Sheets

U.S. PATENT DOCUMENTS

| | | | |
|---|---|---|---|
| 2004/0066262 A1* | 4/2004 | Wenner | 335/205 |
| 2004/0176684 A1 | 9/2004 | Tabuchi et al. | |
| 2005/0063906 A1* | 3/2005 | Kraizer et al. | 424/9.1 |
| 2005/0143623 A1 | 6/2005 | Kojima | |
| 2007/0010709 A1 | 1/2007 | Reinschke | |
| 2007/0104755 A1* | 5/2007 | Sterling et al. | 424/423 |

FOREIGN PATENT DOCUMENTS

| | | |
|---|---|---|
| JP | 2004-248956 A | 9/2004 |
| JP | 2005-508668 | 4/2005 |
| JP | 2005-508668 A | 4/2005 |
| JP | 2005-185567 | 7/2005 |
| JP | 2005-192632 A | 7/2005 |
| JP | 2006-142013 | 6/2006 |
| JP | 2006-149689 | 6/2006 |
| JP | 2006-239413 | 9/2006 |
| WO | WO 03/090618 A2 | 11/2003 |

OTHER PUBLICATIONS

Japanese Office Action dated Mar. 5, 2013 in Japanese Patent Application No. 2009-501324.

* cited by examiner

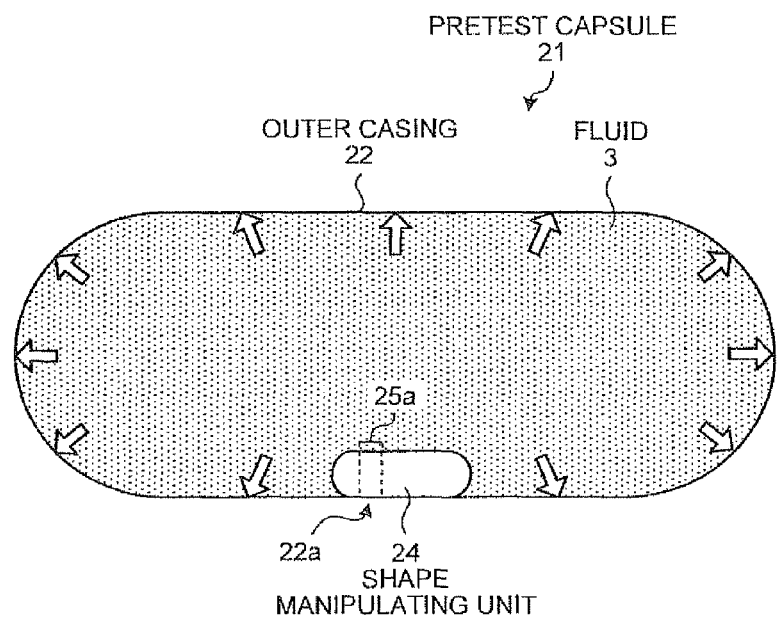
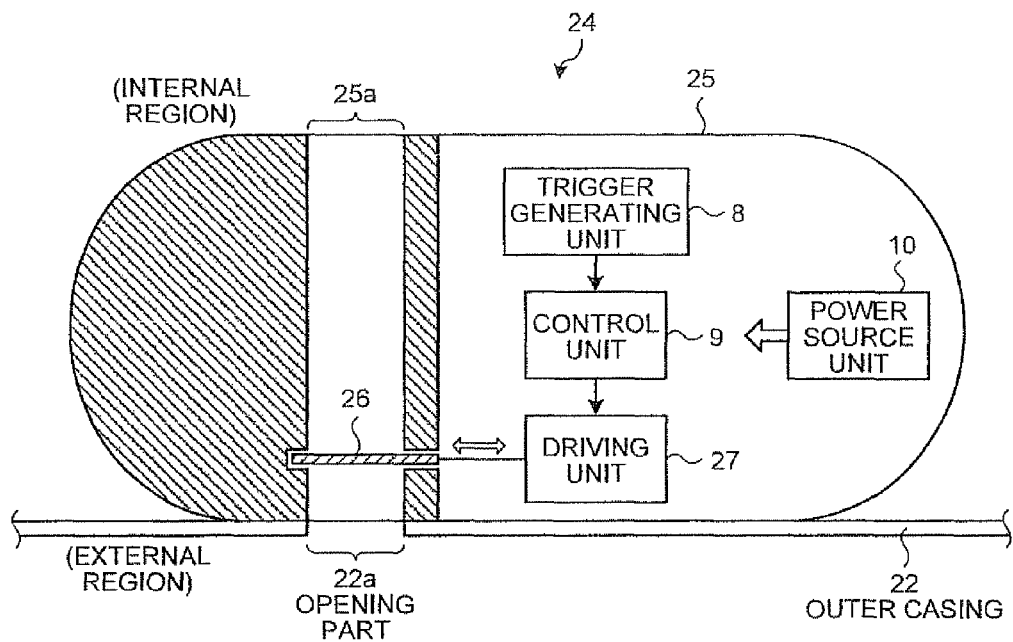

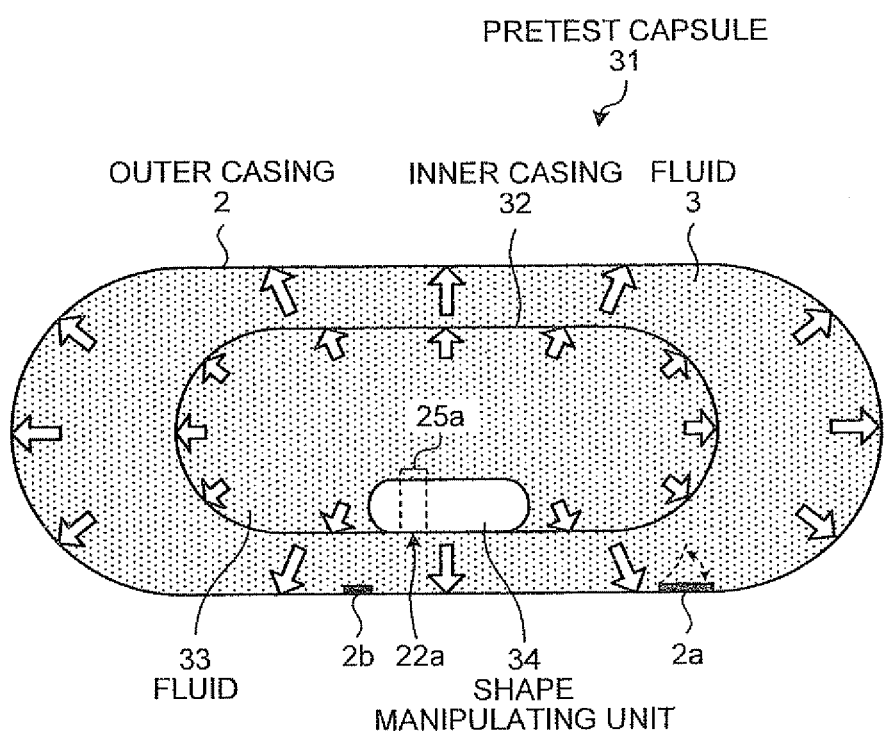

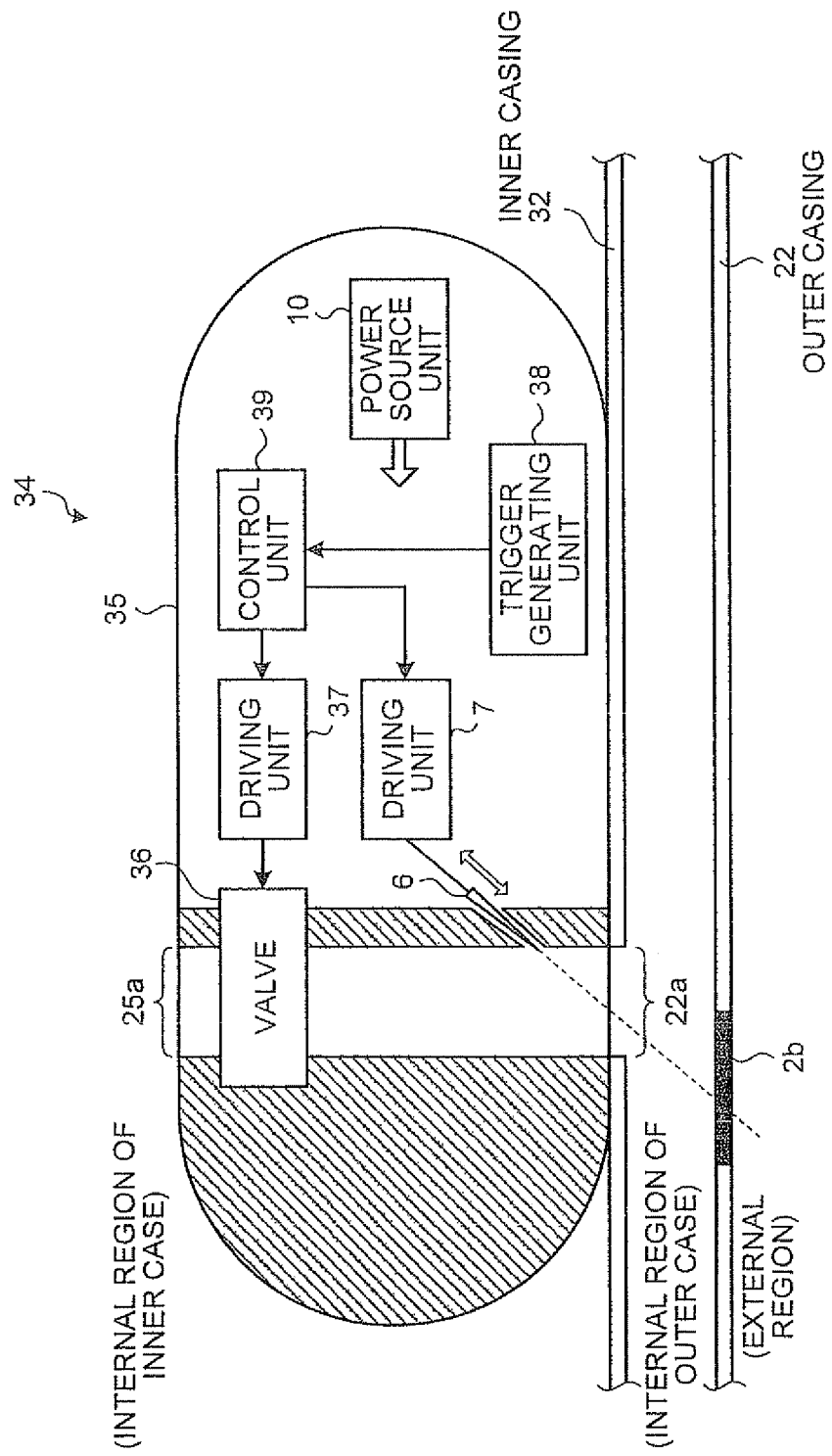

PRETEST CAPSULE 41
OUTER CASING 42
SHAPE MANIPULATING UNIT 44
44c
A 41
42
44b
THROUGH HOLE 44c
A
44a
44b } 44
3 FLUID

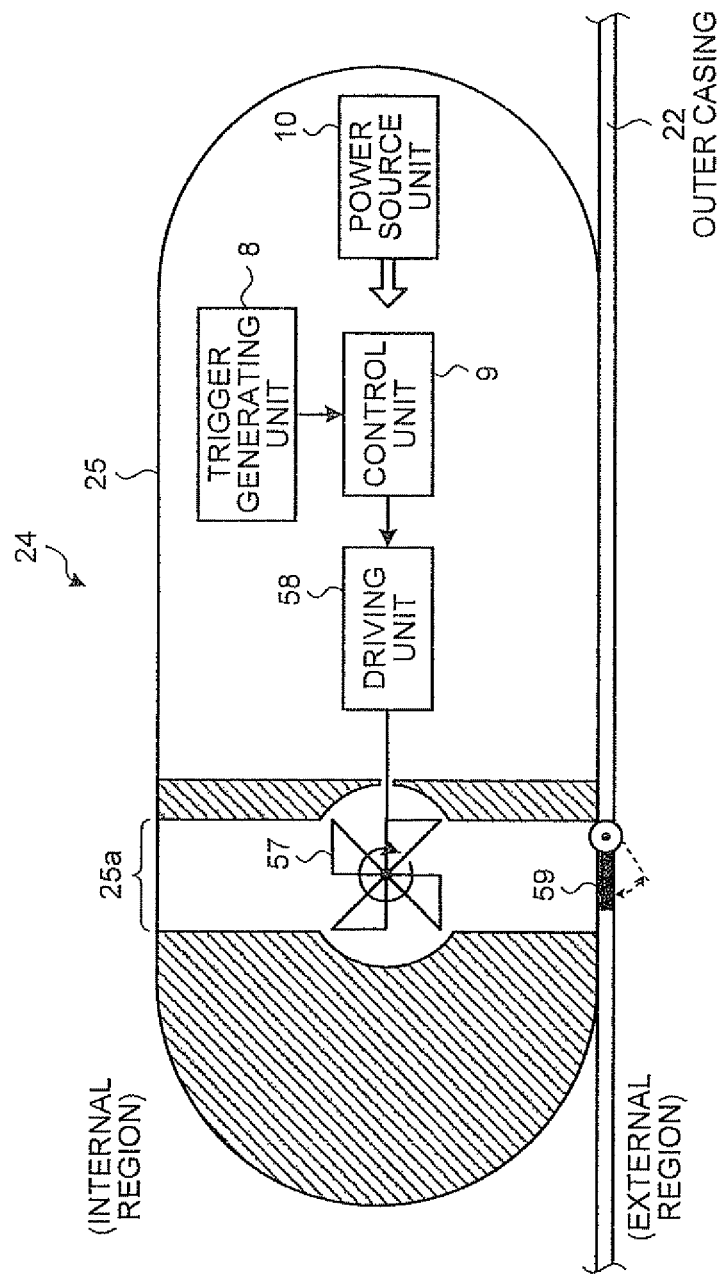

LUMEN PASSABILITY CHECKING DEVICE, LUMEN PASSABILITY CHECKING METHOD, AND METHOD OF MANUFACTURING LUMEN PASSABILITY CHECKING DEVICE

CROSS-REFERENCE TO RELATED APPLICATIONS

This application is a continuation of PCT international application Ser. No. PCT/JP2008/053678 filed on Feb. 29, 2008 which designates the United States, incorporated herein by reference, and which claims the benefit of priority from Japanese Patent Application No. 2007-051969, filed on Mar. 1, 2007, incorporated herein by reference.

BACKGROUND OF THE INVENTION

1. Field of the Invention

The present invention relates to a lumen passability checking device inserted into an organ of a subject to check beforehand whether a capsule medical device inserted into the organ of the subject such as a patient can pass through inside of a lumen of the subject (that is, a lumen passability of a capsule medical device), a lumen passability checking method, and a method of manufacturing a lumen passability checking device.

2. Description of the Related Art

Capsule endoscopes having an imaging function and a radio communication function have been produced in the field of endoscope in recent years. A subject such as a patient ingests the capsule endoscope from his mouth to perform a capsule endoscope examination to observe (examine) the inside of an organ. After the patient ingests the capsule, the capsule endoscope moves within organs such as stomach and small intestine by a peristaltic movement or the like until when the capsule endoscope is naturally excreted from the subject. During this period, the capsule endoscope sequentially captures images within the organ of the subject (hereinafter, also referred to as "in-vivo images") at 0.5-second intervals, for example, The capsule endoscope sequentially radio-transmits the captured in-vivo images to a receiving device carried by the subject.

The receiving device carried by the subject sequentially receives the in-vivo images that are radio-transmitted by the capsule endoscope, and sequentially accumulates the in-vivo images within a recording medium of the receiving device. Thereafter, the recording medium that stores an in-vivo image group of the subject is detached from the receiving device, and is attached to a predetermined image display device. The image display device acquires the in-vivo image group of the subject via the recording medium, and displays the in-vivo image group of the subject on a display. A doctor or nurse observes the in-vivo images displayed in the image display device, and performs a diagnosis of the subject.

When a stenosis part exists within an organ (within a lumen) of a subject, a capsule endoscope taken into the subject to perform the capsule endoscope examination tends to be stagnated at the stenosis part. Therefore, before performing the capsule endoscope examination on the subject, a doctor or nurse needs to check a passability of the capsule endoscope, to be taken into the subject, through a lumen. As a device that checks a passability of the capsule endoscope through the lumen (that is, lumen passability checking device), there has been a device formed by an external coating and an internal filling material, and when the device stagnates at a stenosis part within the lumen, the device collapses the external coating and discharges the internal filling material to the inside of the lumen, and marks (colors) the stenosis part by a marker included in the discharged internal filling material (see Published Japanese translation of a PCT application No. 2005-508668).

SUMMARY OF THE INVENTION

A lumen passability checking device according to an aspect of the present invention includes: an expandable and shrinkable outer casing that contains a predetermined fluid, is expanded by a pressure of the contained fluid, and forms an external diameter substantially equal to that of a capsule medical device to be inserted into a body of a subject; and a shape manipulating unit that flows out the fluid contained in the outer casing to shrink-deform the outer casing, wherein the outer casing is shrink-deformed by flowing out the fluid, while maintaining a state of being integrated with the shape manipulating unit.

A lumen passability checking method according to another aspect of the present invention, for inserting into a body of a subject a lumen passability checking device that forms an external diameter substantially equal to that of a capsule medical device to be inserted into the body of the subject and for checking a lumen passability of the capsule medical device within the body of the subject, includes: communicating, within the body of the subject, inside and outside of an expandable and shrinkable outer casing of the lumen passability checking device, the outer casing being expanded by a pressure of a fluid and forming the external diameter substantially equal to that of the capsule medical device; and shrink-deforming the outer casing by flowing out the fluid from the outer casing, the inside and outside of which are communicated at the communicating.

A method of manufacturing a lumen passability checking device according to still another aspect of the present invention, for checking a lumen passability of a capsule medical device to be inserted into a body of a subject, includes: arranging at an opening part of an expandable and shrinkable outer casing, a structure having an external diameter smaller than that of the capsule medical device, the structure formed with an openable and closable through hole and a dissoluble unit that can be dissolved by a substance in the body of the subject, closing the opening part of the outer casing, inserting a duct member into the through hole of the structure, injecting a fluid into the outer casing via the duct member, expanding the outer casing by a pressure of the fluid, and setting an external diameter of the outer casing to an external diameter substantially equal to that of the capsule medical device.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a schematic vertical cross-sectional view for depicting a configuration example of a pretest capsule according to a third embodiment of the present invention;

FIG. 8 is a block diagram for schematically depicting a configuration example of a shape manipulating unit of the pretest capsule according to the third embodiment of the present invention;

FIG. 9 is a schematic vertical cross-sectional view for depicting a configuration example of a pretest capsule according to a fourth embodiment of the present invention;

FIG. 10 is a block diagram for schematically depicting a configuration example of a shape manipulating unit of the pretest capsule according to the fourth embodiment of the present invention;

FIG. 23 is a block diagram for schematically depicting a configuration example of a fifth modification of the shape manipulating unit having a function of switching a communication duct that communicates inside and outside of an outer casing to be a communication state or a blocked state.

DETAILED DESCRIPTION OF THE PREFERRED EMBODIMENTS

Exemplary embodiments of a lumen passability checking device, a lumen passability checking method, and a method of manufacturing a lumen passability checking device according to the present invention will be described below in detail with reference to the accompanying drawings. In the following descriptions, a capsule-shaped device (a pretest capsule) is shown as an example of the lumen passability checking device according to the present invention, and a check (test) of a lumen passability of the capsule medical device until when the device reaches an examination target organ of a subject by using the pretest capsule is described. However, the present invention is not limited to the embodiments.

First Embodiment

Figure 1:
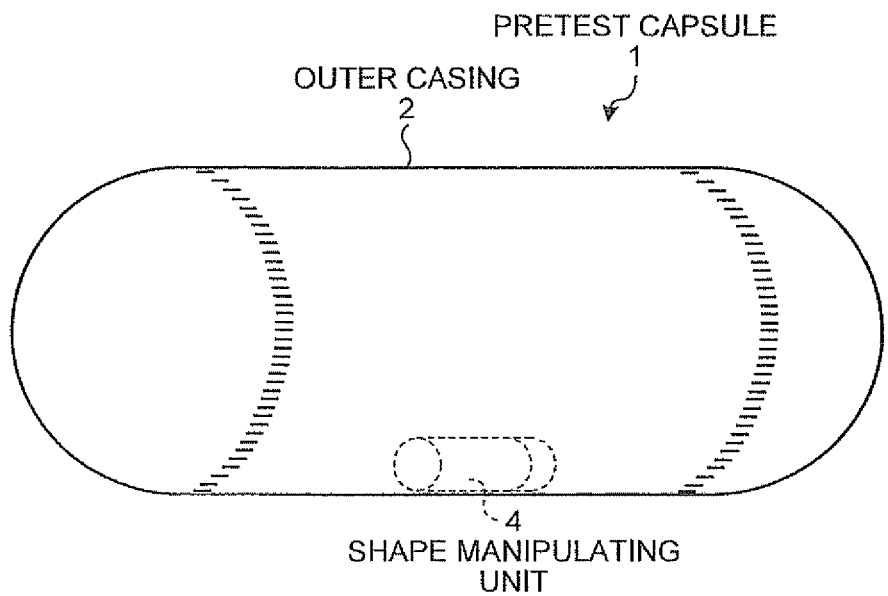
FIG. 1 is an external schematic diagram for depicting a configuration example of a pretest capsule according to a first embodiment of the present invention.
Figure 2:
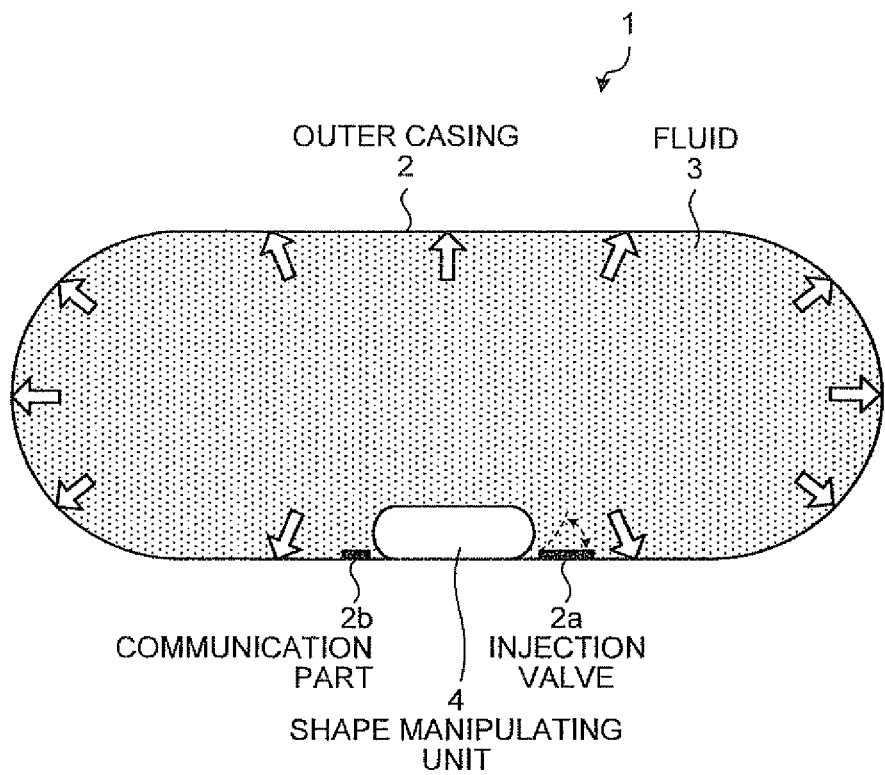
FIG. 2 is a schematic vertical cross-sectional view for exemplifying an internal configuration of the pretest capsule according to the first embodiment of the present invention.

FIG. 1 is an external schematic diagram of a configuration example of a pretest capsule according to a first embodiment of the present invention. FIG. 2 is a schematic vertical cross-sectional view for exemplifying an internal configuration of the pretest capsule according to the first embodiment of the present invention. As shown in FIGS. 1 and 2, a pretest capsule 1 according to the first embodiment includes an expandable and shrinkable outer casing 2 forming an external diameter substantially equal to that of a capsule medical device, a fluid 3 contained in the outer casing 2, and a shape manipulating unit 4 that shrink-deforms the outer casing 2 by flowing out the fluid 3 from the outer casing 2.

The outer casing 2 is embodied by using an elastic member such as latex or silicon rubber, and forms a three-dimensional shape by expansion due to a pressure of the content. Specifically, the outer casing 2 has an injection valve 2a that functions as an injection opening through which the fluid 3 is injected, and contains the fluid 3 flowed in via the injection valve 2a. As shown in FIG. 2, the injection valve 2a has a check valve configuration, permits the flow of the fluid 3 from the outside to the inside of the outer casing 2, and inhibits flow from the inside of the outer casing 2. Therefore, the fluid 3 within the outer casing 2 does not flow out (leak) from the injection valve 2a. The outer casing 2 is expanded by a pressure of the fluid 3 injected via the injection valve 2a, thereby forming an external diameter substantially equal to that of a desired capsule medical device (the capsule medical device subsequently inserted into the organ of the subject). In this case, the outer casing 2 forms a cylindrical three-dimensional shape having this external diameter as a diameter in a radial direction (a direction perpendicular to a longitudinal axis direction). Preferably, the outer casing 2 forms a capsule shape substantially the same as that of the capsule medical device. The outer casing 2 maintains the external diameter (further, an external shape similar to that of the capsule medical device) substantially the same as that of the capsule medical device, due to a pressure of the contained fluid 3.

Also, the outer casing 2 has a communication part 2b that forms a through hole to flow out the fluid 3 at the time of shrink-deforming the outer casing 2. The communication part 2b is formed at one part of the outer casing 2, and a through hole can be formed there without breaking the outer casing 2. Specifically, the communication part 2b is a part made rigid on the expandable and shrinkable outer casing 2, and is usually (for example, before the outer casing 2 is shrink-deformed) in a closed state. On the other hand, a through hole is formed in the communication part 2b by the shape manipulating unit 4 described later, at the time of flowing out the fluid 3 from the outer casing 2 (that is, at the time of shrink-deforming the outer casing 2). In this case, the through hole can be formed in the communication part 2b without breaking the outer casing 2. The through hole formed in the communication part 2b functions as a communication hole to communicate the inside and outside of the outer casing 2, and permits flowing out the fluid 3 to shrink-deform the outer casing 2. That is, the outer casing 2 is shrink-deformed along the flow of the fluid 3 via the through hole of the communication part 2b. The communication part 2b is made rigid to the extent not to interrupt the expansion and contraction (shrink deformation) of the outer casing 2.

The fluid is injected into the outer casing 2 to expand the outer casing 2. Specifically, the fluid 3 is a colorless and transparent gas harmless to a human body, such as air (atmosphere), oxygen, carbon dioxide, nitrogen, and is injected into the outer casing 2 via the injection valve 2a. The fluid 3 injected into the outer casing 2 expands the outer casing 2 as described above by applying a pressure to an internal surface of the outer casing 2, as indicated by a thick-line arrowhead in FIG. 2. The pressure of the fluid 3 within the outer casing 2 is stronger than at least a contraction force of the outer casing 2. When the through hole is not formed in the communication part 2b, even when an external pressure is applied to the outer casing 2 by a peristaltic movement of the organ, the outer casing 2 maintains an external diameter of the outer casing 2 (further, an external shape similar to that of the capsule medical device) substantially the same as that of the capsule medical device.

The shape manipulating unit 4 manipulates a three-dimensional shape of the outer casing 2. Specifically, as shown in FIG. 2r for example, the shape manipulating unit 4 is fixedly arranged near the communication part 2b within the outer casing 2. The shape manipulating unit 4 forms the through hole in the communication part 2b at a desired timing, and flows out the fluid 3 contained in the outer casing 2 to the outside of the outer casing 2 via the through hole. With this arrangement, the shape manipulating unit 4 decreases the pressure of the fluid 3 that expands the outer casing 2, thereby shrink-deforming the outer casing 2. The shape manipulating unit 4 defines an ultimate external diameter (and an ultimate three-dimensional shape) of the outer casing 2 after the outer casing 2 is shrink-deformed.

Figure 3:
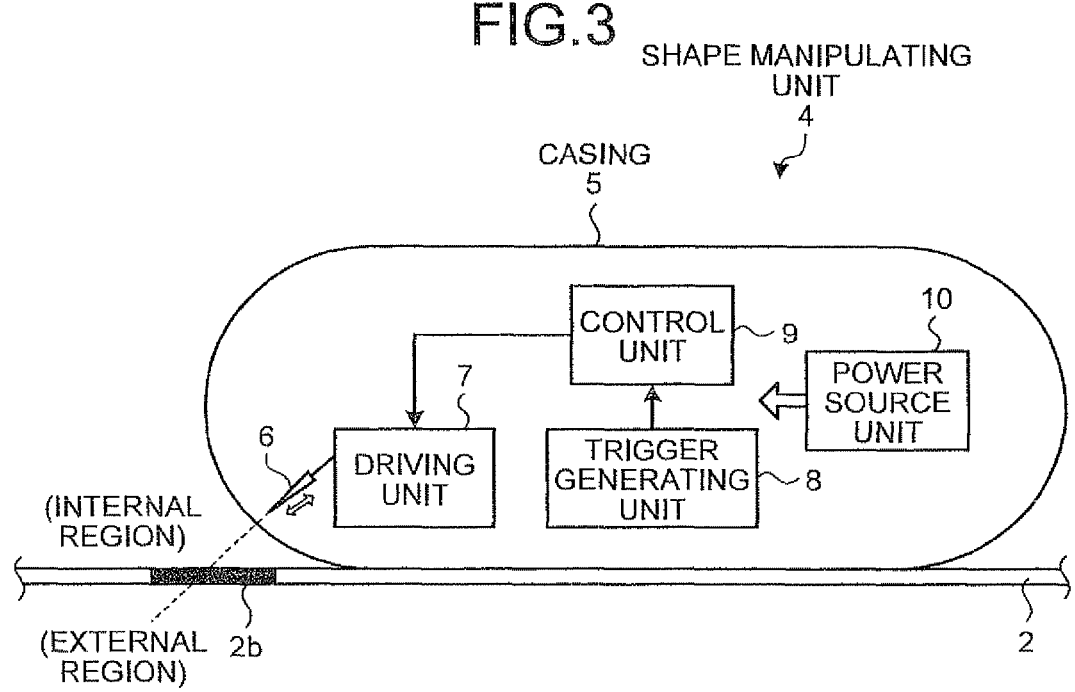
FIG. 3 is a block diagram for schematically depicting a configuration example of a shape manipulating unit of the pretest capsule according to the first embodiment of the present invention.

A configuration of the shape manipulating unit 4 is described in detail next. FIG. 3 is a block diagram for schematically depicting a configuration example of the shape manipulating unit 4 of the pretest capsule 1 according to the first embodiment of the present invention. As shown in FIG. 3, the shape manipulating unit 4 includes a casing 5 having an external diameter smaller than that of the capsule medical device, a needle 6 for forming a through hole in the communication part 2b of the outer casing 2, a driving unit 7 that drives the needle 6, a trigger generating unit 8 that generates a trigger signal at a desired timing, a control unit 9 that controls the driving unit 7 based on the trigger signal, and a power source unit 10 that supplies power to each constituent unit of the shape manipulating unit 4.

The casing 5 is a structure containing each constituent unit (the needle 6, the driving unit 7, the trigger generating unit 8, the control unit 9, and the power source unit 10) of the shape manipulating unit 4, and is fixedly arranged near the communication part 2b within the outer casing 2. The casing 5 has a three-dimensional shape having an external diameter at least smaller than that of the capsule medical device, and preferably has a capsule shape substantially similar to that of the capsule medical device. The casing 5 having this external diameter can pass through the whole region within the lumen from the oral cavity to the anus of the subject even when a barrier such as a stenosis part blocking the advancement of the capsule medical device exists within the lumen. The casing 5 is covered by the outer casing 2, of which diameter is deformed, in a state of closely contacting the internal surface of the outer casing 2 to an external wall surface of the casing 5. The casing 5 is covered by the outer casing 2 in a state of closely contacting the external wall surface of the casing 5 to the internal surface of the outer casing 2, thereby defining an ultimate external diameter and an ultimate three-dimensional shape of the outer casing 2 after the outer casing 2 is shrink-deformed. In this case, the outer casing 2 is in a shrink-deformed state conforming to the external diameter of the casing 5. Consequently, the external diameter of the outer casing 2 becomes substantially equal to the external diameter of the casing 5, and the three-dimensional shape of the outer casing 2 becomes substantially equal to the three-dimensional shape of the casing 5.

The needle 6 is used to form a through hole in the communication part 2b to communicate the inside and outside of the outer casing 2, and is connected to the driving unit 7. At the time of shrink-deforming the outer casing 2, the driving unit 7 drives the needle 6 to form a through hole in the communication part 2b. Specifically, the driving unit 7 is driven based on control of the control unit 9 to insert the needle 6 into an opening part (not shown) of the casing 5 and pierce the needle 6 through the casing 5 and stick the needle 6 into the communication part 2b. Thereafter, the driving unit 7 accommodates the needle 6, which has stuck on the communication part 2b, within the casing 5. As a result of the driving unit 7 reciprocally moving the needle 6 in this way, the needle 6 forms in the communication part 2b a through hole to communicate an internal region and an external region of the outer casing 2. The needle 6 and the driving unit 7 form the through hole in the communication part 2b, and function as a communication mechanism of flowing out the fluid 3 from the outer casing 2 by communicating the inside and outside of the outer casing 2.

The trigger generating unit 8 generates a trigger to trigger shrink deformation of the outer casing 2 at a desired timing. Specifically, the trigger generating unit 8 has a timer function, for example, and is set with a desired time in advance. The trigger generating unit 8 measures the time, generates a trigger signal at a timing after a lapse of a predetermined time (that is, at a desired timing), and transmits the generated trigger signal to the control unit 9. The trigger signal generated by the trigger generating unit 8 is a trigger to form a through hole in the communication part 2b at a desired timing to communicate the inside and outside of the outer casing 2. That is, the trigger signal triggers shrink deformation of the outer casing 2 at a desired timing.

The trigger generating unit 8 can start measuring the time when power is supplied by the power source unit 10. Alternatively, the trigger generating unit 8 can have a receiving unit that receives a radio signal, and start measuring the time when the receiving unit receives a radio signal transmitted from the outside. In either case, the trigger generating unit 8 can start measuring the time after the subject orally ingests the pretest capsule 1. As a result, a trigger signal can be generated at timing when a predetermined time has elapsed after the pretest capsule 1 is inserted into the organ of the subject.

The control unit 9 controls the driving unit 7 to shrink-deform the outer casing 2 at a desired timing. Specifically, the control unit 9 receives a trigger signal generated at a predetermined timing by the trigger generating unit 8, and controls the driving unit 7 based on the received trigger signal. In this case, the control unit 9 reciprocally moves the needle 6 to control the driving unit 7 to form a through hole in the communication part 2b of the outer casing 2 as described above. By controlling the driving unit 7 in this way, the control unit 9 can communicate the inside and outside of the outer casing 2 at a desired timing. As a result, the control unit 9 can shrink-deform the outer casing 2 at a desired timing.

The power source unit 10 can be embodied by using a small storage battery such as a capacitor, for example, and supplies power to the driving unit 7, the trigger generating unit 8r and the control unit 9. The power source unit 10 has an optical switch or a magnetic switch not particularly shown, and switches between on and off states in reaction with light of a predetermined wave band such as infrared rays or an external magnetic field. The power source unit 10 can supply power to the driving unit 7, the trigger generating unit 8, and the control unit 9 in the on state. The power source unit 10 is also embodied by using a resonant circuit formed by using a coil and a capacitor, and can convert an external magnetic field into power, and supply the converted power to the driving unit 7, the trigger generating unit 8, and the control unit 9.

The shape manipulating unit 4 having such a configuration shrink-deforms the outer casing 2 by flowing out the fluid 3 from the outer casing 2 at a desired timing, while maintaining the above state being contained in the outer casing 2. That is, the outer casing 2 is shrink-deformed by flowing out the fluid 3, while maintaining the state of being integrated with the shape manipulating unit 4 due to the operation of the shape manipulating unit 4. In this case, the outer casing 2 is shrink-deformed conforming to the external diameter of the casing 5 of the shape manipulating unit 4.

Figure 4:
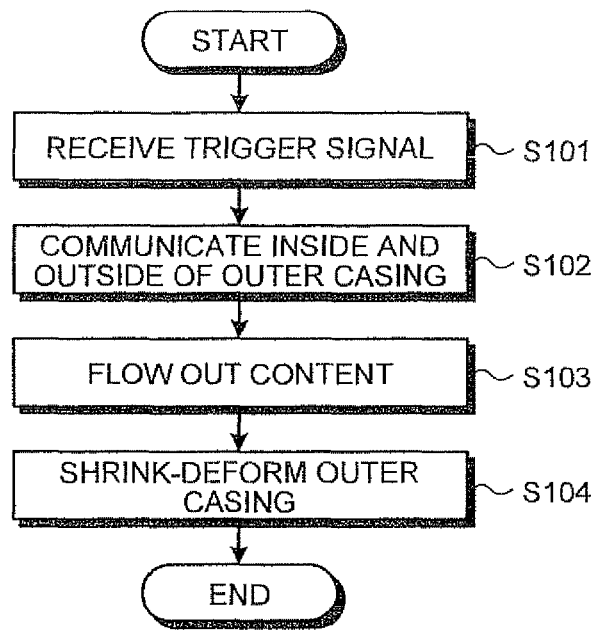
FIG. 4 is a flowchart for exemplifying a process procedure of a control unit of the shape manipulating unit that shrink-deforms an outer casing at a desired timing.

The operation of the shape manipulating unit 4 that shrink-deforms the outer casing 2 is described next. FIG. 4 is a flowchart for exemplifying a process procedure of the control unit 9 of the shape manipulating unit 4 that shrink-deforms the outer casing 2 at a desired timing. When the shape manipulating unit 4 shrink-deforms the outer casing 2 at a desired timing, the control unit 9 performs the process procedure exemplified in FIG. 4.

Specifically, as shown in FIG. 4, the control unit 9 receives a trigger signal generated at a desired timing by the trigger generating unit 8 (Step S101), and communicates the inside and outside of the outer casing based on the received trigger signal (Step S102). At Steps S101 and S102, the trigger generating unit 8 transmits the trigger signal to the control unit 9 to trigger the shrink deformation of the outer casing 2. When the control unit 9 is triggered by the trigger signal to shrink-deform the outer casing 2, the control unit 9 controls the driving unit 7 to stick the needle 6 into the communication part 2b of the outer casing 2, thereby forming a through hole in the communication part 2b. The control unit 9 forms the through hole in the communication part 2b in this way to communicate the inside and outside of the outer casing 2.

By communicating the inside and outside of the outer casing 2 in this way, the control unit 9 flows out the content, i.e., the fluid 3, of the outer casing 2 (Step S103), and shrink-deforms the outer casing 2 along the flow of the fluid 3 (Step S104). In this case, the fluid 3 flows out from the through hole of the communication part 2b to the outside of the outer casing 2 by the shrinkage of the outer casing 2, and decreases a pressure applied to the outer casing 2 (a pressing force of expanding the outer casing 2). The outer casing 2 shrinks due to reduction of the pressure of the fluid 3, and is finally shrink-deformed conforming to the external diameter of the casing 5 of the shape manipulating unit 4.

Figure 5:
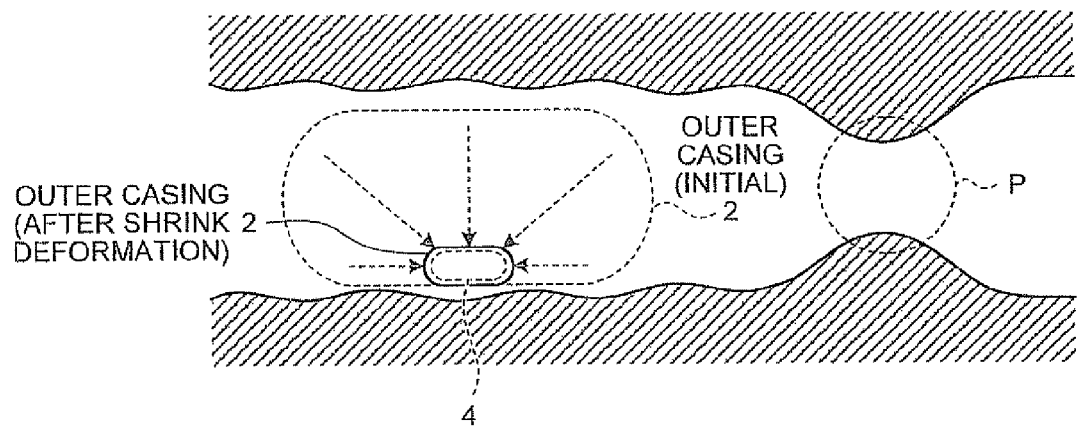
FIG. 5 is a schematic diagram for explaining shrink deformation of the outer casing of the pretest capsule according to the first embodiment of the present invention.

Shrink deformation of the outer casing 2 of the pretest capsule 1 according to the first embodiment of the present invention is described next. FIG. 5 is a schematic diagram for explaining the shrink deformation of the outer casing 2 of the pretest capsule 1 according to the first embodiment of the present invention.

The subject orally ingests the pretest capsule 1 before orally ingesting the capsule medical device to check a passability of the capsule medical device through the lumen of the subject. The pretest capsule 1 orally ingested by the subject advances within the lumen of the subject by a peristaltic movement or the like. When a barrier such as a stenosis part that blocks advancement of the capsule medical device exists within the lumen of the subject, the pretest capsule 1 cannot pass through the passage barrier, and consequently, is stagnated within the lumen. In this case, the pretest capsule 1 shrink-deforms the outer casing 2 at a desired timing, while maintaining a state of integration with the shape manipulating unit 4. As a result, the pretest capsule 1 can easily pass through the passage barrier.

Specifically, as shown in FIG. 5, when the outer casing 2 is in an initial state (that is, a state of forming a capsule shape having an external diameter substantially equal to that of the capsule medical device), the pretest capsule 1 cannot pass through a stenosis part P as an example of a passage barrier blocking the advancement of the capsule medical device, and stagnates there. The outer casing 2 of the pretest capsule 1 is shrink-deformed based on the operation of the shape manipulating unit 4 while flowing out the fluid 3 from the through hole of the communication part 2b. In this case, the outer casing 2 is continuously shrunk, while maintaining a state of containing the shape manipulating unit 4 (that is, a state of being integrated with the shape manipulating unit 4), and is finally shrink-deformed in a state of having the external diameter substantially equal to that of the shape manipulating unit 4 from the initial state of having the external diameter substantially equal to that of the capsule medical device.

The outer casing 2 that is shrink-deformed in this way, while maintaining the state of being integrated with the shape manipulating unit 4 can form a three-dimensional shape (specifically, a capsule shape) having an external diameter substantially equal to that of the shape manipulating unit 4 without scattering broken pieces or remainders of the outer casing 2 within the lumen. Thereafter, the outer casing 2 and the shape manipulating unit 4 after being shrink-deformed (that is, the shrink-deformed pretest capsule 1) can easily pass through the stenosis part P, and are naturally excreted from the body of the subject together with a bodily waste without leaving broken pieces or remainders of the outer casing 2 within the lumen.

Meanwhile, the fluid 3 flowing out and separated from the outer casing 2 when the outer casing 2 is shrink-deformed easily passes through the passage barrier such as the stenosis part P, and is easily excreted from the body of the subject. Therefore, after checking the passability of the capsule medical device through the lumen of the subject, the fluid 3 hardly remains within the lumen of the subject, and does not interrupt various organ examinations to examine the inside of the organ of the subject by having the subject orally ingested the capsule medical device. The fluid 3 can be a gas harmless to a human body, and is preferably a colorless and transparent gas as described above. This is for the following reason. When the fluid 3 is colorless and transparent, it is possible to securely prevent the interruption, attributable to the fluid, of various organ examinations performed by having the subject orally ingested the capsule medical device, even when the fluid 3 remains within the lumen of the subject after checking the lumen passability of the capsule medical device.

As described above, the shape manipulating unit 4 shrink-deforms the outer casing 2 at timing when a desired time set in advance in the trigger generating unit 8 passes. When the time required for the capsule medical device orally ingested by the subject to sequentially pass through the inside of the organ and reach a desired examination target organ is set in the trigger generating unit 8 as a desired time, the shape manipulating unit 4 can shrink-deform the outer casing 2 at the timing when the desired time set in the trigger generating unit 8 passes, that is, at a timing (that is, a desired timing) when a time usually necessary for the pretest capsule 1, orally ingested by the subject, to reach the desired examination target organ passes. Even when a passage barrier such as a stenosis part exists within the lumen of the subject leading to the desired examination target organ, the shape manipulating unit 4 can prevent the pretest capsule 1 from being excessively stagnated within the lumen due to the passage barrier, by shrink-deforming the outer casing 2 at the desired timing.

For example, when the time required for the capsule medical device orally ingested by the subject to sequentially pass through the inside of the lumen and reach large intestine, as the examination target organ, is set in the trigger generating unit 8, the shape manipulating unit 4 can shrink-deform the outer casing 2 at a timing when a time usually necessary for the pretest capsule 1, orally ingested by the subject, to reach the large intestine (a time to reach the large intestine) passes. The shape manipulating unit 4 can prevent the pretest capsule 1 from being excessively stagnated within the lumen by shrink-deforming the outer casing 2 at a timing when the large intestine reaching time has elapsed, even when the pretest capsule 1 cannot reach the large intestine due to a passage barrier such as a stenosis part existing within the lumen (small intestine, for example) of the subject leading to the desired examination target organ.

The desired timing when the shape manipulating unit 4 shrink-deforms the outer casing 2, that is, a desired time to be set in advance in the trigger generating unit 8, is not limited to the time necessary for the capsule medical device or the pretest capsule 1 to reach the desired examination target organ after the device or the pretest capsule 1 is orally ingested. The desired timing can be a time necessary to check a passability of the capsule medical device through the lumen of the subject, or can be a minimum necessary time to keep the pretest capsule 1 within the lumen of the subject.

After the subject orally ingests the pretest capsule 1 having the above configuration to check the lumen passability of the capsule medical device, the pretest capsule 1 is stagnated at a passage barrier when the passage barrier such as a stenosis part exists within the lumen of the subject. In this case, even when a predetermined time has elapsed after the subject orally ingests the pretest capsule 1, a user (an examiner) such as a doctor or nurse cannot detect the pretest capsule 1 supposed to be excreted from the body of the subject. Based on this fact, the user determines that there is a problem in the passability of the capsule medical device through the lumen of the subject (that is, because the passage barrier such as a stenosis part exists within the lumen, the capsule medical device is difficult to reach the desired examination target organ).

The pretest capsule 1 stagnated within the lumen of the subject shrink-deforms the outer casing 2 at a desired timing without scattering broken pieces or remainders of the outer casing 2, and is naturally excreted from the body of the subject together with a bodily waste, as described above.

On the other hand, when there is no passage barrier such as a stenosis part within the lumen of the subject, the pretest capsule 1 reaches a reach target region (that is, a desired examination target organ) of the capsule medical device to be inserted into the body of the subject by a peristaltic movement or the like, and is thereafter excreted from the body of the subject together with a bodily waste. In this case, a user can detect the pretest capsule 1 excreted from the body of the subject by the time when a predetermined time has elapsed after the subject orally ingests the pretest capsule 1. Based on this fact, the user determines that there is no problem in the passability of the capsule medical device through the lumen of the subject (that is, the capsule medical device orally ingested by the subject sequentially passes through the inside of the lumen, and can reach the desired examination target organ).

For the capsule medical device to be inserted into the organ of the subject, there can be listed a capsule endoscope having an imaging function and a radio communication function, a capsule pH-measuring device that measures pH within a living body, a capsule drug dosing device having a function of dispersing or injecting a drug into a living body, and a capsule collection device for collecting a substance within a living body.

As described above, in the first embodiment of the present invention, the pretest capsule includes an expandable and shrinkable outer casing containing a fluid, and a shape manipulating unit that manipulates a three-dimensional shape of the outer casing. The outer casing is expanded by a pressure of the contained fluid, thereby forming a three-dimensional shape having an external diameter substantially equal to that of the desired capsule medical device. The shape manipulating unit flows out the fluid from the outer casing that forms the three-dimensional shape, thereby shrink-deforming the outer casing. The outer casing is configured to be shrink-deformed due to reduction of the pressure due to flow of the fluid, while maintaining a state that the outer casing is integrated with the shape manipulating unit. Therefore, at the time of checking a lumen passability of the capsule medical device until when the capsule medical device reaches a target organ (an organ to be examined) within the subject, a three-dimensional shape of the outer casing having the external diameter substantially equal to that of the capsule medical device can be maintained within the lumen. After the passability of the capsule medical device through the lumen of the subject is checked, the outer casing can be shrink-deformed to have a three-dimensional shape having an external diameter smaller than that of the capsule medical device, without scattering broken pieces or remainders of the outer casing within the lumen. As a result, there is achieved a lumen passability checking device, in which a passability of the capsule medical device through the lumen of the subject until when the device reaches the target organ within the subject can be checked. After the lumen passability of the capsule medical device is checked, the lumen passability checking device can be easily excreted from the body of the subject.

Further, the shape manipulating unit shrink-deforms the outer casing at the timing when a desired time set in advance in the shape manipulating unit passes. Therefore, the outer casing can be shrink-deformed at the timing (that is, a desired timing) when the desired time has elapsed after the subject orally ingests the lumen passability checking device (the pretest capsule) according to the present invention. As a result, a stagnation time of the lumen passability checking device within the lumen of the subject can be minimized, and even when a passage barrier such as a stenosis part exists within the lumen of the subject, excessive stagnation of the lumen passability checking device within the lumen due to the passage barrier can be prevented.

Further, the outer casing has an external diameter substantially to the same as that of the capsule medical device to be inserted into the subject, and is also expanded to form a three-dimensional shape (that is, a capsule shape) substantially similar to that of the capsule medical device. Therefore, a passability of the capsule medical device through the lumen of the subject can be checked in a condition similar to a state that the capsule medical device is actually inserted into the body of the subject.

The expandable and shrinkable outer casing is expanded to have an external diameter substantially the same as that of the capsule medical device and to form a three-dimensional shape similar to that of the capsule medical device. Therefore, various three-dimensional shapes and external diameters can be easily formed by the outer casing. As a result, lumen passability checking devices having various three-dimensional shapes can be easily prepared flexibly corresponding to capsule medical devices having various three-dimensional shapes. Consequently, a lumen passability of capsule medical devices having various three-dimensional shapes can be easily checked.

Second Embodiment

A second embodiment of the present invention is described next. In the first embodiment, the external diameter of the outer casing 2 is maintained by the pressure of the fluid 3 contained in the outer casing 2. On the other hand, in the second embodiment, the outer casing 2 further includes therein a supporting member that supports the outer casing 2 in a radial direction of. The external diameter of the outer casing 2 is maintained by a supporting force of the supporting member and the pressure of the fluid 3.

Figure 6:
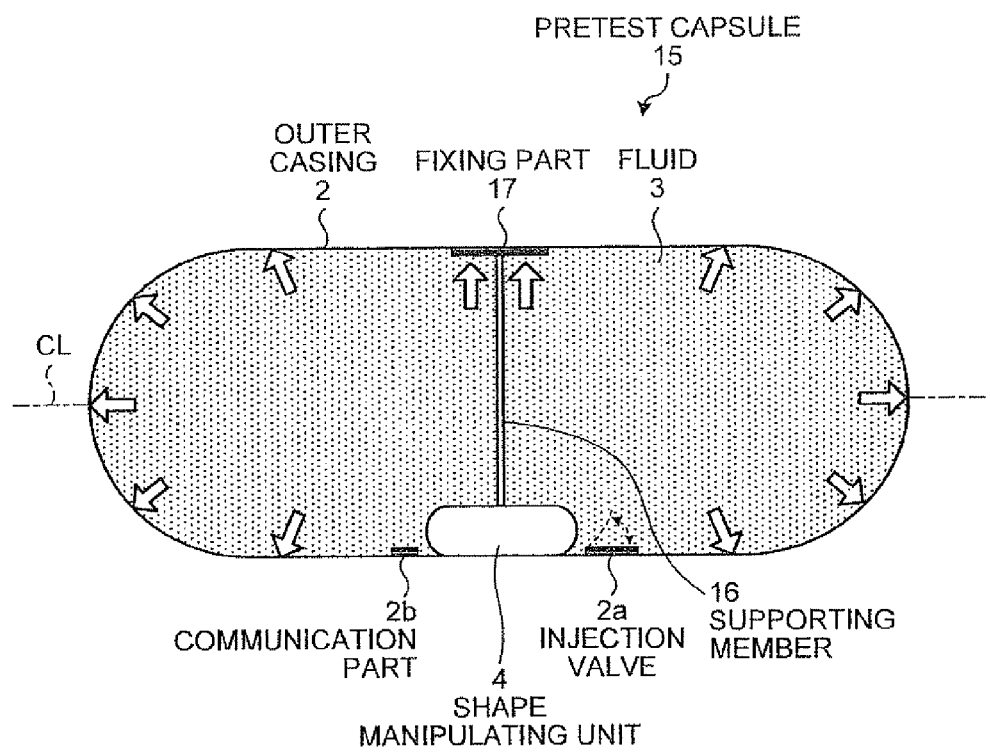
FIG. 6 is a schematic vertical cross-sectional view for depicting a configuration example of a pretest capsule according to a second embodiment of the present invention.

FIG. 6 is a schematic vertical cross-sectional view of a configuration example of a pretest capsule according to the second embodiment of the present invention. As shown in FIG. 6, a pretest capsule 15 according to the second embodiment further includes a supporting member 16 that supports the outer casing 2 in a radial direction, and a fixing part 17 that fixes the supporting member 16, within the outer casing 2 similar to that of the pretest capsule 1 according to the first embodiment. Other configurations are the same as those of the first embodiment, and like constituent elements are denoted by like reference numerals.

The supporting member 16 is a member that supports the three-dimensionally shaped outer casing 2 in a direction perpendicular to a center axis CL of the outer casing 2 in a longitudinal direction (that is, a radial direction of the outer casing 2). As shown in FIG. 6, the supporting member 16 is arranged within the outer casing 2 (preferably, near the center of the center axis CL within the outer casing 2). In this case, one end of the supporting member 16 is fixed to the shape manipulating unit 4 (specifically, the casing 5), and the other end of the supporting member 16 is fixed to the fixing part 17. The fixing part 17 is provided at a position opposed to the shape manipulating unit 4 on an internal surface of the outer casing 2. The supporting member 16 having both ends connected to the fixing part 17 and the shape manipulating unit 4, respectively, applies a supporting force to the outer casing 2 in a radial direction via the shape manipulating unit 4 and the fixing part 17. The supporting member 16 reinforces a radial direction component of the pressure of the fluid 3 (that is, the pressure of the fluid 3 in the radial direction of the outer casing 2) by the supporting force.

Further, when the pressure of the fluid 3 (that is, a pressing force by the fluid 3 pressing the outer casing 2 from the inside) decreases due to flow of the fluid 3 from the outer casing 2, the supporting member 16 is shrink-deformed in the radial direction of the outer casing 2 along reduction of the pressure of the fluid 3. That is, a supporting force F1 of the supporting member 16 is a weak force as compared with a contractive force F2 of the outer casing 2 in a radial direction present in the outer casing 2 in a state of forming an external diameter substantially equal to that of the capsule medical device. The supporting member 16 having the supporting force F1 does not block shrink deformation of the outer casing 2. A pressing force F3 in a radial direction due to the pressure of the fluid 3 contained in the outer casing 2 is equal to the contractive force F2 in the radial direction of the outer casing 2.

The outer casing 2 applied with the supporting force F1 of the supporting member 16 and the pressing force F3 of the fluid 3 from the inside can reinforce the force in a radial direction against an external force applied to the outer casing 2 by a peristaltic movement or the like, thereby firmly maintaining the external diameter substantially equal to that of the capsule medical device. The pretest capsule 15 further including the supporting member 16 can suppress an unintentional shrink deformation of the outer casing 2 by the external force by a peristaltic movement or the like. As a result, a passability of the capsule medical device through the lumen of the subject can be checked with higher precision.

The above-described supporting member 16 can be a bar-shaped member or a sheet-shaped member, or a spring member having a bar shape, a sheet shape, or a coil shape, as far as the supporting member has (or has a potential of) the supporting force F1 weaker than the contractive force F2 of the outer casing 2. Alternatively, the supporting member 16 can be a shape memory member such as an SMA coil that is expanded or shrunk when heated to a predetermined temperature or above. At the time of shrink-deforming the outer casing 2, the shape memory member can be shrunk in a radial direction by heating this member to a predetermined temperature or above or by cooling this member to a predetermined temperature or below.

As described above, in the second embodiment of the present invention, the outer casing further includes therein a supporting member that supports the outer casing (that is, the outer casing expanded by the fluid) in a radial direction, which forms an external diameter substantially equal to that of a desired capsule medical device. Other configurations are set similar to those of the first embodiment. Therefore, the second embodiment has operational effects similar to that of the first embodiment. At the same time, in the second embodiment, the force in a radial direction against the external force applied to the outer casing can be reinforced. Accordingly, an external diameter substantially equal to that of the capsule medical device can be maintained more firmly. As a result, an unintentional shrink deformation of the outer casing by a peristaltic movement or the like can be suppressed, and a passability of the capsule medical device through the lumen of the subject can be checked with higher precision.

Third Embodiment

A third embodiment of the present invention is described next. In the first embodiment, the inside and outside of the outer casing 2 are communicated by forming a through hole in the communication part 2b of the outer casing 2. On the other hand, in the third embodiment, a communication duct that communicates the inside and outside of an outer casing is formed on a casing of a shape manipulating unit. A communication state and a blocked state between the inside and outside of the outer casing are switched via the communication duct.

FIG. 7 is a schematic vertical cross-sectional view of a configuration example of a pretest capsule according to the third embodiment of the present invention. As shown in FIG. 7, a pretest capsule 21 according to the third embodiment includes an outer casing 22 in place of the outer casing 2 of the pretest capsule 1 according to the first embodiment, and includes a shape manipulating unit 24 in place of the shape manipulating unit 4. Other configurations are the same as those of the first embodiment, and like constituent elements are denoted by like reference numerals.

The outer casing 22 is embodied by using an elastic member such as latex or silicon rubber. The outer casing 22 is expanded by a pressure of the fluid 3 similarly to the outer casing 2 of the pretest capsule 1 according to the first embodiment, and forms a three-dimensional shape having an external diameter substantially equal to that of a desired capsule medical device (preferably, a capsule shape substantially similar to that of the capsule medical device). Meanwhile, the outer casing 22 does not have the injection valve 2a and the communication part 2b (see FIG. 2), unlike the outer casing 2 of the first embodiment. The outer casing 22 lets in or flows out the fluid 3 via a communication duct 25a of the shape manipulating unit 24 described later, instead of the injection valve 2a and the through hole of the communication part 2b. That is, the outer casing 22 contains the shape manipulating unit 24 having the communication duct 25a in place of the shape manipulating unit 4 in the first embodiment, and has an opening part 22a that communicates to the communication duct 25a of the contained shape manipulating unit 24. The outer casing 22 lets in or flows out the fluid 3 via the communication duct 25a of the shape manipulating unit 24 communicating to the opening part 22a, and is shrunk along flow of the fluid 3 via the communication duct 25a. In this case, the outer casing 22 is finally shrink-deformed conforming to the external diameter of the shape manipulating unit 24.

The shape manipulating unit 24 has the communication duct 25a to communicate the inside and outside of the outer casing 22. The communication duct 25a is fixedly arranged within the outer casing 2 in a state that the communication duct 25a and the opening part 22a communicate. In this case, an external surface of the shape manipulating unit 24 (an external wall surface of a casing 25 described later) and at least a periphery of the opening part 22a of the outer casing 22 are fixed, thereby preventing the opening part 22a from inducing breaking of the outer casing 22. The shape manipulating unit 24 can change a state of the communication duct 25a between a blocked state and a communication state at a desired timing. When the communication duct 25a is switched to the communication state, the fluid 3 within the outer casing 22 is flowed out from the outer casing 22 via the communication duct 25a. Accordingly, the shape manipulating unit 24 shrink-deforms the outer casing 22 by decreasing the pressure of the fluid 3 that expands the outer casing 22. The shape manipulating unit 24 defines an ultimate external shape (and further, an ultimate three-dimensional shape) of the outer casing 22 after the outer casing 22 is shrink-deformed, similarly to the shape manipulating unit 4 in the first embodiment.

A configuration of the shape manipulating unit 24 is described next in detail. FIG. 8 is a block diagram for schematically depicting a configuration example of the shape manipulating unit 24 of the pretest capsule 21 according to the third embodiment of the present invention. As shown in FIG. 8, the shape manipulating unit 24 includes the casing 25 in place of the casing 5 of the shape manipulating unit 4 (see FIG. 3) in the first embodiment, includes a blocking member 26 of the communication duct 25a in place of the needle 6, and includes a driving unit 27 of the blocking member 26 in place of the driving unit 7. The control unit 9 of the shape manipulating unit 24 controls drive of the driving unit 27 (a switch drive of the blocking member 26 that blocks the communication duct 25a) based on a trigger signal generated at a desired timing by the trigger generating unit 8, and switches between the communication state and the blocked state of the inside and outside of the outer casing 22 via the communication duct 25a through the drive control of the driving unit 27. Other configurations are the same as those of the first embodiment, and identical constituent parts are assigned with like identical numerals.

The casing 25 is a structure containing constituent units of the shape manipulating unit 24 (the blocking member 26, the driving unit 27, the trigger generating unit 8, the control unit 9, and the power source unit 10), and has the communication duct 25a. The casing 25 is fixedly arranged within the outer casing 22 in a state of communicating the communication duct 25a and the opening part 22a. In this case, the external wall surface of the casing 25 is fixed to at least the periphery of the opening part 22a on an internal surface of the outer casing 22. The casing 25 has a three-dimensional shape at least having an external diameter smaller than that of the capsule medical device, and preferably has a capsule shape substantially similar to that of the capsule medical device. The casing 25 is covered by the outer casing 22 in a state that the external wall surface of the casing 25 is closely contacted to the internal surface of the outer casing 22 similarly to the casing 5 of the shape manipulating unit 4 in the first embodiment, thereby defining an ultimate external diameter and an ultimate three-dimensional shape of the outer casing 22 after shrink deformation. In this case, the outer casing 22 is in a state of being shrink-deformed conforming to the external diameter of the casing 25. The external diameter of the outer casing 22 becomes substantially equal to the external diameter of the casing 25, and the three-dimensional shape of the outer casing 22 becomes substantially equal to the three-dimensional shape of the casing 25.

The blocking member 26 is a sheet-shaped member that closes the communication duct 25a communicating the inside and outside of the outer casing 22 (that is, blocks the communication between the inside and outside of the outer casing 22 via the communication duct 25a), and is connected to the driving unit 27. The driving unit 27 is driven based on the control of the control unit 9, thereby opening or closing the blocking member 26. In this case, the driving unit 27 opens the blocking member 26 at timing when a desired time set in advance in the trigger generating unit 8 passes (that is, at a desired timing similar to that of the first embodiment). The driving unit 27 switches the blocked state of the communication duct 25a to the communication state at a desired timing by opening at a desired timing the blocking member 26 in a closed state of the communication duct 25a. As a result, an internal region and an external region of the outer casing 22 become in the communication state via the communication duct 25a at a desired timing. When the inside and outside of the outer casing 22 are communicating via the communication duct 25a, the fluid 3 passes through the communication duct 25a and flows out from the outer casing 22. The blocking member 26 and the driving unit 27 function as a communication mechanism that switches at a desired timing the state of the communication duct 25a that communicates the inside and outside of the outer casing 22 to be the communication state or the blocked state.

The driving unit 27 can close the blocking member 26 based on the control of the control unit 9, thereby switching a state of the communication duct 25a from the communication state to the blocked state at a desired timing. In this case, the shape manipulating unit 24 further includes a receiving unit (not shown) that receives a control signal from the outside. The control unit 9 can acquire via the receiving unit the control signal transmitted from the outside at timing when a required quantity of the fluid 3 is injected into the outer casing 22 via the communication duct 25a. Based on the acquired control signal, the control unit 9 can cause the driving unit 27 to close the blocking member 26. On the other hand, a sealing member such as an O-ring can be provided on the surface of the blocking member 26 or a sliding path of the blocking member 26, thereby preventing the fluid 3 from leaking out from the communication duct 25a in the blocked state.

The shape manipulating unit 24 having such a configuration flows out the fluid 3 from the outer casing 22 at a desired timing, while maintaining a state of being contained in the outer casing 22, thereby shrink-deforming the outer casing 22. That is, the outer casing 22 is shrink-deformed by flowing out the fluid 3, while maintaining a state of integration with the shape manipulating unit 24, based on the operation of the shape manipulating unit 24. In this case, the control unit 9 of the shape manipulating unit 24 causes the driving unit 27 to open the blocking member 26 to communicate the inside and outside of the outer casing 22, in place of forming a through hole by the needle 6, at Step S102 described above.

As described above, in the third embodiment of the present invention, a communication duct that communicates the inside and outside of the outer casing is formed in a casing of a shape manipulating unit. A communication state and a blocked state of the communication duct are switched to each other at a desired timing. A fluid is flowed out from the outer casing via the communication duct that is switched to the communication state. The outer casing is shrink-deformed along the flow of the fluid via the communication duct, and other configurations of the third embodiment are set similar to those of the first embodiment. Therefore, operational effects similar to those of the first embodiment can be achieved, and a communication path that communicates the inside and outside of the outer casing can be formed easier than a through hole formed on the outer casing.

The fluid can be injected into the outer casing or the fluid can be flowed out from the outer casing via one communication duct. Therefore, an injection valve of a check valve structure to inject the fluid into the outer casing and a communication part to form a through hole to flow out the fluid from the outer casing do not need to be formed on the outer casing. As a result, the lumen passability checking device according to the present invention can be manufactured more easily.

Fourth Embodiment

A fourth embodiment of the present invention is described next. In the first embodiment, the outer casing 2 is continuously shrink-deformed conforming to the external diameter of the casing 5 of the shape manipulating unit 4 (that is, an ultimate external diameter). On the other hand, in the fourth embodiment, the outer casing 2 further contains an inner casing forming an external diameter smaller than that of the outer casing 2. The outer casing 2 is shrink-deformed at two stages of: a first-stage shrink deformation conforming to the external diameter of the inner casing; and a second-stage shrink deformation conforming to the external diameter of the casing of the shape manipulating unit.

FIG. 9 is a schematic vertical cross-sectional view of a configuration example of a pretest capsule 31 according to the fourth embodiment of the present invention. As shown in FIG. 9, the pretest capsule 31 according to the fourth embodiment further has an expandable and shrinkable inner casing 32 containing a fluid 33 within the outer casing 2 of the pretest capsule 1 according to the first embodiment, and has a shape manipulating unit 34 in place of the shape manipulating unit 4. In this case, the shape manipulating unit 34 has the communication duct 25a similar to that of the shape manipulating unit 24 in the third embodiment, and is fixedly arranged within the inner casing 32 in a state of communicating the opening part 22a formed on the inner casing 32 and the communication duct 25a. The outer casing 2 performs in a step-wise manner the first-stage shrink deformation (hereinafter, "first shrink deformation") of being shrunk conforming to an external diameter of the inner casing 32, and the second-stage shrink deformation (hereinafter, "second shrink deformation") of being shrunk conforming to an external diameter of the shape manipulating unit 34. Other configurations are the same as those of the first embodiment, and like constituent elements are denoted by like reference numerals.

The inner casing 32 is embodied by using an elastic member such as latex or silicon rubber, and forms a three-dimensional shape by expansion due to a pressure of the content. Specifically, the inner casing 32 contains the shape manipulating unit 34 having the communication duct 25a, and the fluid 33 injected via the communication duct 25a. The inner casing 32 is expanded by the pressure of the contained fluid 33, and forms an external diameter smaller than that of the outer casing 2 and larger than that of the shape manipulating unit 34. That is, the external diameter of the inner casing 32 is substantially equal to that of a small-sized capsule medical device smaller than a capsule medical device having an external diameter simulated by the outer casing 2. The external diameter of the shape manipulating unit 34 is smaller than that of the small-sized capsule medical device. In this case, the inner casing 32 forms a cylindrical three-dimensional shape having an external diameter substantially equal to that of the small-sized capsule medical device as a diameter in a radial direction.

The inner casing 32 is fixedly arranged within the outer casing 2, while maintaining an external diameter and a three-dimensional shape substantially equal to those of the small-sized capsule medical device due to the pressure of the fluid 33 contained. The inner casing 32 contained in the outer casing 2 defines an external diameter and a three-dimensional shape of the outer casing after the first-stage shrink deformation. Specifically, the inner casing 32 is covered by the outer casing 2 in a state that an external surface of the inner casing 32 is closely contacted to the internal surface of the outer casing 2, thereby defining the external diameter and the three-dimensional shape of the outer casing 2. In this case, the outer casing 2 is in a state of being shrink-deformed (that is, the first shrink deformation) conforming to the external diameter of the inner casing 32. The external diameter and the three-dimensional shape of the outer casing 2 in this state are substantially equal to those of the inner casing 32.

Further, the inner casing 32 contains the shape manipulating unit 34 as described above, and flows out the fluid 33 via the communication duct 25a of the shape manipulating unit 34 contained. The inner casing 32 is shrunk along the flow out of the fluid 33, and is finally shrink-deformed conforming to the external diameter of the shape manipulating unit 34. In this case, the outer casing 2 after the first shrink deformation is shrunk together with the inner casing 32, while maintaining a state of being superimposed on the inner casing 32, and is finally shrink-deformed (the second shrink deformation) conforming to the external diameter of the shape manipulating unit 34. When the outer casing 2 is second-shrink-deformed in this way, the inner casing 32 is in a state of being superimposed on an external wall surface of the shape manipulating unit 34, and the outer casing 2 is in a state of being superimposed on the external surface of the inner casing 32. That is, an external diameter and a three-dimensional shape of the outer casing 2 after the second shrink deformation, an ultimate external diameter and an ultimate three-dimensional shape of the inner casing 32 after the shrink deformation, and an external diameter and a three-dimensional shape of the shape manipulating unit 34 are substantially equal, respectively.

Preferably, the inner casing 32 forms an external diameter substantially equal to that of a small-sized capsule medical device due to a pressure of the fluid 33, and forms a capsule shape substantially the same as that of the small-sized capsule medical device. When this capsule medical device is substantially similar to the small-sized capsule medical device, it is preferable that the inner casing 32 is substantially similar to that of the outer casing 2 forming a three-dimensional shape substantially similar to the capsule medical device.

The fluid 33 is injected into the inner casing 32 to expand the inner casing 32. Specifically, the fluid 33 is a gas similar to the fluid 3, and is a colorless and transparent gas harmless to a human body such as air (atmosphere), oxygen, carbon dioxide, and nitrogen. The fluid 33 is injected into the inner casing 32 via the communication duct 25*a* of the shape manipulating unit 34 contained by the inner casing 32. The fluid 33 injected into the inner casing 32 expands the inner casing 32 as described above by applying a pressure to the internal surface of the inner casing 32, as shown by a thick arrowhead in FIG. 9. The pressure of the fluid 33 within the inner casing 32 is stronger than at least a contraction force of the inner casing 32. When the communication duct 25*a* described above is in a blocked state, even if an external pressure is applied to the inner casing 32 by a peristaltic movement of the organ, an external diameter of the inner casing 32 substantially equal to that of the small-sized capsule medical device (and further, an external shape similar to that of a small-sized capsule medical device) can be maintained.

The shape manipulating unit 34 has the communication duct 25*a* to communicate the inside and outside of the inner casing 32, and is fixedly arranged within the inner casing 32 in a state that the communication duct 25*a* and the opening part 22*a* of the inner casing 32 are communicating. In this case, an external surface of the shape manipulating unit 34 (an external wall surface of a casing 35 described later) and at least a periphery of the opening part 22*a* of the inner casing 32 are fixed, thereby preventing the opening part 22*a* from inducing breaking of the inner casing 32.

Further, similarly to the shape manipulating unit 4 in the first embodiment, the shape manipulating unit 34 forms a through-hole (that is, a through hole that communicates the inside and outside of the outer casing 2) at a desired timing in the communication part 2*b* of the outer casing 2. The shape manipulating unit 34 flows out the fluid 3 contained in the outer casing 2 to the outside of the outer casing 2 via the through hole. With this arrangement, the shape manipulating unit 34 first-shrink-deforms the outer casing 2 by decreasing the pressure of the fluid 3 that expands the outer casing 2. The shape manipulating unit 34 can switch a state of the communication duct 25*a* between the blocked state and the communication state at a desired timing. By changing a state of the communication duct 25*a* to the communication state, the shape manipulating unit 34 flows out the fluid 33 from within the inner casing 32 to the outside of the inner casing 32 via the communication duct 25*a*. With this arrangements the shape manipulating unit 34 shrink-deforms the inner casing 32 by decreasing the pressure of the fluid 33 that expands the inner casing 32. In this case, the shape manipulating unit 34 second-shrink-deforms the outer casing 2 together with the inner casing 32. The shape manipulating unit 34 defines an ultimate external diameter and an ultimate three-dimensional shape of the inner casing 32 after the shrink deformation, and an ultimate external diameter and an ultimate three-dimensional shape of the outer casing 2 after the second shrink deformation, similarly to the shape manipulating unit 4 in the first embodiment.

A configuration of the shape manipulating unit 34 is described next in detail. FIG. 10 is a block diagram for schematically depicting a configuration example of the shape manipulating unit 34 of the pretest capsule 31 according to the fourth embodiment of the present invention. As shown in FIG. 10, the shape manipulating unit 34 includes the casing 35 formed with the communication duct 25*a* in place of the casing 5 of the shape manipulating unit (see FIG. 3) in the first embodiment, includes a trigger generating unit 38 that generates a trigger in a step-wise manner in place of the trigger generating unit 8, and includes a control unit 39 in place of the control unit 9. The shape manipulating unit 34 further includes a valve 36 that opens and closes the communication duct 25*a*, and a driving unit 37 that drives the valve 36. Other configurations are the same as those of the first embodiment, and like constituent elements are denoted by like reference numerals.

The casing 35 is a structure containing constituent units of the shape manipulating unit 34 (the needle 6, the driving units 7 and 37, the trigger generating unit 8, the control unit 39, and the power source unit 10), and has the communication duct 25*a*. The casing 35 is fixedly arranged within the inner casing 32 in a state of communicating the communication duct 25*a* and the opening part 22*a* of the inner casing 32. In this case, the external wall surface of the casing 35 is fixed to at least the periphery of the opening part 22*a* on an internal surface of the inner casing 32. The casing 35 has a three-dimensional shape having an external diameter smaller than that of a small-sized capsule medical device having an external diameter simulated by the inner casing 32, and preferably has a capsule shape substantially similar to that of a desired capsule medical device. The casing 35 is covered by the inner casing 32 in a state that the external wall surface of the casing 35 is closely contacted to the internal surface of the inner casing 32, and is also covered by the outer casing 2 in a state of being in close contact with the internal surface of the outer casing 2 via the inner casing 32. With this arrangement, an ultimate external diameter and an ultimate three-dimensional shape of the inner casing 32 after the shrink deformation, and an ultimate external diameter and an ultimate three-dimensional shape of the outer casing 2 after the second shrink deformation are defined. In this case, the external diameter and the three-dimensional shape of the outer casing 2 after the second shrink deformation, the ultimate external diameter and the ultimate three-dimensional shape of the inner casing 32 after the shrink deformation, and the external diameter and the three-dimensional shape of the shape manipulating unit 34 become substantially equal to each other as described above.

The valve 36 switches a state of the communication duct 25*a*, which communicates the inside and outside of the inner casing 32, to the communication state and the blocked state, and the valve 36 is connected to the driving unit 37. The driving unit 37 is driven based on the control of the control unit 39, and opens or closes the valve 36. In this case, the driving unit 37 opens the valve 36 at a timing (a desired timing of second-shrink-deforming the outer casing 2) after a desired time set in advance in the trigger generating unit 38 passes. The driving unit 37 opens at a desired timing the valve 36 in a closed state of the communication duct 25a, thereby switching the blocked state of the communication duct 25a to the communication state at a desired timing. As a result, the inside and outside of the inner casing 32 are in the communication state via the communication duct 25a at a desired timing.

At the timing when the driving unit 37 opens the valve 36 (that is, the timing of communicating the inside and outside of the inner casing 32), a through hole for communicating the inside and outside of the outer casing 2 is already formed in the communication part 2b of the outer casing 2 by the needle 6. Specifically, the driving unit 7 reciprocally moves the needle 6 at a desired timing before the timing of communicating the inside and outside of the inner casing 32, based on the control of the control unit 39. In this case, the needle 6 sticks the communication part 2b of the outer casing 2 through the casing 35 and the opening part 22a, and is accommodated in the casing 35 thereafter. As a result, a through hole communicating the inside and outside of the outer casing 2 is formed in the communication part 2b at a desired timing before communicating the inside and outside of the inner casing 32.

Therefore, when the driving unit 37 opens the valve 36 to switch the state of the communication duct 25a to the communication state, the inside and outside of the inner casing 32 are in communication to each other via the communication duct 25a and the through hole of the communication part 2b. In this case, the fluid 33 within the inner casing 32 flows sequentially through the communication duct 25a and the through hole of the communication part 2b, and flows out.

The needle 6, the valve 36, and the driving units 7 and 37 function as a communication mechanism that communicates the inside of the outer casing 2 to the outside at a first-stage desired timing, and flows out the fluid 3 from within the outer casing 2, and that communicates the inside of the inner casing 32 to the outside at a second-stage desired timing after the first-stage desired timing, and flows out the fluid 33 from within the inner casing 32.

The driving unit 37 can change a state of the communication duct 25a from the communication state to the blocked state at a desired timing by closing the valve 36 based on the control of the control unit 39. In this case, the shape manipulating unit 34 can further include a receiving unit (not shown) that receives a control signal from the outside. The control unit 39 can acquire a control signal transmitted from the outside via the receiving unit at a timing when a necessary amount of the fluid 33 is injected into the inner casing 32 via the communication duct 25a, and can cause the driving unit 37 to close the valve 36 based on the acquired control signal.

The trigger generating unit 38 sequentially generates plural triggers to shrink-deform the outer casing 2 in a step-wise manner at plural desired timings. Specifically, the trigger generating unit 38 has a timer function, for example, and is set with plural desired times in advance. The trigger generating unit 38 measures a time similarly to the trigger generating unit 8 of the shape manipulating unit 4 in the first embodiment, and also sequentially generates trigger signals at timings (that is, desired timings) after a lapse of the desired time set in advance, each time when the time elapses. The trigger generating unit 38 sequentially transmits the generated trigger signals to the control unit 39. More specifically, when a first desired time has elapsed among the preset plural desired times, the trigger generating unit 38 generates a first trigger signal that requests communication between the inside and outside of the outer casing 2 (that is, triggers shrink deformation of the outer casing 2), and transmits the generated first trigger signal to the control unit 39. Thereafter, when a second desired time has elapsed after the first desired time, the trigger generating unit 38 generates a second trigger signal that requests communication between the inside and outside of the inner casing 32 (that is, triggers shrink deformation of the inner casing 32). The trigger generating unit 38 transmits the generated second trigger signal to the control unit 39.

The first trigger signal among the plural trigger signals generated by the trigger generating unit 38 is a first-stage trigger that triggers the first shrink deformation of the outer casing 2 at the first-stage desired timing (hereinafter, "first timing" and the second trigger signal is a second-stage trigger that triggers the second shrink deformation of the outer casing 2 at the second-stage desired timing (hereinafter, "second timing") later than the first timing.

The control unit 39 controls the driving units 7 and 37 to shrink-deform the outer casing 2 in a step-wise manner at plural desired timings. Specifically, the control unit 39 receives the first trigger signal generated at the first timing by the trigger generating unit 38, and controls the driving unit 7 based on the received first trigger signal. In this case, the control unit 39 controls the driving unit to reciprocally move the needle 6 to 7 so as to form a through hole in the communication part 2b of the outer casing 2. By controlling the driving unit 7 in this way, the control unit 39 can communicate the inside and outside of the outer casing 2 at the first timing. As a result, the control unit 39 can first-shrink-deform the outer casing 2 at this first timing. Thereafter, the control unit 39 receives the second trigger signal generated at the second timing by the trigger generating unit 38, and controls the driving unit 37 based on the received second trigger signal. In this case, the control unit 39 controls the driving unit 37 to open the valve 36 and switch a state of the communication duct 25a from the blocked state to the communication state. By controlling the driving unit 37 in this way, the control unit 39 can communicate the inside and outside of the inner casing 32 at the second timing. As a result, the control unit 39 can shrink-deform the inner casing 32 together with the outer casing 2 at this second timing, that is, can second-shrink-deform the outer casing 2.

At each time of receiving a trigger signal (the first trigger signal and the second trigger signal) generated by the trigger generating unit 38, the control unit 39 repeatedly performs a process procedure substantially the same as that at Steps S101 to S104 described above (see FIG. 4). That is, when receiving the first trigger signal, the control unit 39 controls the driving unit 7 to communicate the inside and outside of the outer casing 2 at Step S102, and thereafter, at Step S103, flows out the fluid 3 from within the outer casing 2. At Step S104, the control unit 39 first-shrink-deforms the outer casing 2. On the other hand, when receiving the second trigger signal, the control unit 39 controls the driving unit 37 to communicate the inside and outside of the inner casing 32 at Step S102, and thereafter, at Step S103, flows out the fluid 33 from within the inner casing 32. At Step S104, the control unit 39 second-shrink-deforms the outer casing 2 together with the inner casing 32.

The shape manipulating unit 34 having such a configuration flows out the fluids 3 and 33 from the outer casing 2 or the inner casing 32 at the first timing and second timing, while maintaining a state of being contained in the outer casing 2 via the inner casing 32, thereby shrink-deforming the outer casing 2 at multiple stages.

Figure 11:
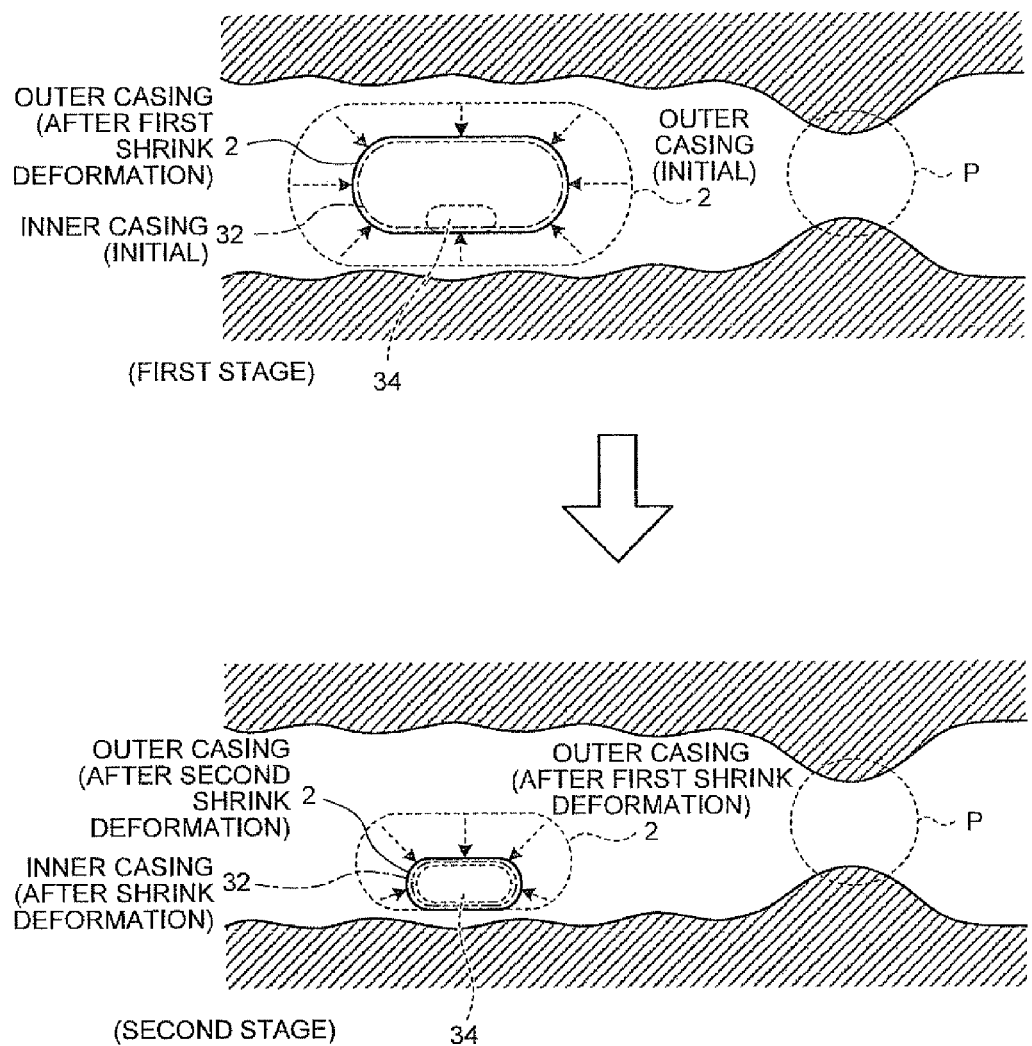
FIG. 11 is a schematic diagram for explaining multiple-stage shrink deformation performed by an outer casing of the pretest capsule according to the fourth embodiment of the present invention.

A multiple-stage shrink deformation performed by the outer casing 2 of the pretest capsule 31 according to the fourth embodiment is described next in detail. FIG. 11 is a schematic diagram for explaining the multiple-stage shrink deformation performed by the outer casing 2 of the pretest capsule according to the fourth embodiment of the present invention.

The subject orally ingests the pretest capsule 31 before orally ingesting the capsule medical device, to check a passability of the capsule medical device through the lumen of the subject, similarly to the first embodiment. The pretest capsule 31 orally ingested by the subject advances through the inside of the lumen of the subject by a peristaltic movement or the like. When a passage barrier such as a stenosis part exists within the lumen of the subject, the pretest capsule 31 is stagnated within the lumen without being able to pass through the passage barrier.

Specifically, as shown in FIG. 11, when the outer casing 2 is in the initial state (that is, a state of forming a capsule shape having an external diameter substantially equal to that of the capsule medical device), the pretest capsule 31 cannot pass through the stenosis part P within the lumen, and is stagnated there. The outer casing 2 of the pretest capsule 31 is first-shrink-deformed based on a first-stage operation of the shape manipulating unit 34 while flowing out the fluid 3 from the through hole of the communication part 2b at the first timing. In this case, the outer casing 2 is continuously shrunk, while maintaining a state of containing the shape manipulating unit 34 together with the inner casing 32 (that is, a state of being integrated with the shape manipulating unit 34), and is shrink-deformed (that is, the first-shrink-deformed) in a state of having the external diameter substantially equal to that of the inner casing 32 from the initial state.

When the outer casing 2 is first-shrink-deformed, the inner casing 32 maintains an external diameter substantially equal to that of a small-sized capsule medical device having an external diameter smaller than that of a capsule medical device having an external diameter simulated by the outer casing 2.

On the other hand, when the stenosis part P is a passage barrier that also blocks the advancement of the small-sized capsule medical device (that is, a capsule medical device having an external diameter simulated by the inner casing 32), the pretest capsule 31 after the first shrink deformation described above cannot pass through the stenosis part P, and stagnates there. The outer casing 2 of the pretest capsule 31 after the first shrink deformation described above is second-shrink-deformed while flowing out the fluid 33 at the second timing based on a second-stage operation of the shape manipulating unit 34. In this case, the inner casing 32 is shrink-deformed together with the outer casing 2 conforming to the external diameter of the shape manipulating unit 34 while flowing out the fluid 33 from the communication duct 25a at the second timing. The outer casing 2 is continuously shrunk, while maintaining a state of containing the shape manipulating unit 34 together with the inner casing 32 (that is, a state of being integrated with the shape manipulating unit 34), and is finally shrink-deformed (that is, the second shrink deformation) in a state of having the external diameter substantially equal to that of the shape manipulating unit 34 from the state after the first shrink deformation.

The outer casing 2 that is first-shrink-deformed and second-shrink-deformed in this way, while maintaining the state of being integrated with the shape manipulating unit 34 can sequentially form a three-dimensional shape (specifically, a capsule shape similar to that of the small-sized capsule medical device) having an external diameter substantially equal to that of the inner casing 32 in the expanded state, and a three-dimensional shape (specifically, a capsule shape) having an external diameter substantially equal to that of the shape manipulating unit 34, without scattering broken pieces or remainders of the outer casing 2 within the lumen. Thereafter, the pretest capsule 31 after the first shrink deformation or the second shrink deformation (specifically, the outer casing 2, the inner casing 32, and the shape manipulating unit 34) can easily pass through the stenosis part P by a peristaltic movement or the like, and finally, they are naturally excreted from the body of the subject together with a bodily waste without leaving broken pieces or remainders of the outer casing 2 within the lumen.

The fluid 33 that flows out when the inner casing 32 is shrink-deformed easily passes through the passage barrier such as the stenosis part P similarly to the fluid 3, and is easily excreted from the body of the subject. Therefore, the fluid 33 hardly remains within the lumen of the subject after a passability of the capsule medical device through the lumen of the subject is checked. The fluid 33 does not interrupt various examinations within organs for examining the inside of the organs of the subject by having the subject ingested the capsule medical device. The fluid 33 can be a gas harmless to a human body similarly to the fluid 3, and is preferably a colorless and transparent gas as described above.

On the other hand, when a time necessary for the capsule medical device orally ingested by the subject to pass through a desired examination target organ is set as the first desired time among plural desired times set in advance in the trigger generating unit 38 of the shape manipulating unit 34, the shape manipulating unit 34 can first-shrink-deform the outer casing 2 at the first timing when the first desired time set in the trigger generating unit 38 passes, that is, at the timing when a time usually necessary for the pretest capsule 31 orally ingested by the subject to pass through the desired examination target organ passes. Further, the shape manipulating unit 34 can second-shrink-deform the outer casing 2 at the second timing when the second desired time set in the trigger generating unit 38 (time after the first desired time) passes, for example, at a timing when a predetermined time has elapsed since the pretest capsule 31 orally ingested by the subject is stagnated within the lumen due to a passage barrier such as the stenosis part P. The shape manipulating unit 34 can prevent the pretest capsule 31 from being excessively stagnated within the lumen due to the passage barrier, by shrink-deforming the outer casing 2 in a step-wise manner at the desired timings (the first or second timing), even when the passage barrier such as a stenosis part exists within the lumen of the subject leading to the desired examination target organ.

After the subject orally ingests the pretest capsule 31 having the above configuration to check a lumen passability of a predetermined capsule medical device, the pretest capsule 31 is stagnated due to a passage barrier such as a stenosis part when the passage barrier exists within the lumen of the subject. In this case, a user (an examiner) such as a doctor or nurse cannot detect the pretest capsule 31 supposed to be excreted from the body of the subject even when a predetermined time has elapsed since the subject orally ingests the pretest capsule 31. Based on this fact, the user determines that there is a problem in the passability of the predetermined capsule medical device through the lumen of the subject (that is, because the passage barrier such as a stenosis part exists within the lumen, it is difficult to have the predetermined capsule medical device reached the desired examination target organ).

The pretest capsule 31 stagnated within the lumen of the subject first-shrink-deforms the outer casing 2 at the first timing. In this case, an external diameter of the pretest capsule 31 after the first shrink deformation (specifically, an external diameter of the outer casing 2 after the first shrink deformation) is substantially equal to that of a small-sized capsule medical device having an external diameter smaller than that of the predetermined capsule medical device of which external diameter is simulated by the outer casing 2 in the initial state. When the user cannot detect the first-shrink-deformed pretest capsule 31 supposed to be excreted from the body of the subject even after a lapse of a further predetermined time since the predetermined time has elapsed, the user determines that there is a problem in the passability of the small-sized capsule medical device through the lumen of the subject (that is, it is difficult to have the small-sized capsule medical device reached the desired examination target organ). On the other hand, when the user detects the first-shrink-deformed pretest capsule 31 excreted from the body of the subject, the user determines that there is no problem in the passability of the small-sized capsule medical device through the lumen of the subject (that is, it is possible to have the small-sized capsule medical device reached the desired examination target organ).

The pretest capsule 31 stagnated within the lumen of the subject first-shrink-deforms and second-shrink-deforms the outer casing 2 at a desired timing without scattering broken pieces or remainders of the outer casing 2 within the lumen, and is naturally excreted from the body of the subject together with a bodily waste.

On the other hand, when a passage barrier such as a stenosis part does not exist within the lumen of the subject, the pretest capsule 31 reaches, by a peristaltic movement or the like, a desired examination target organ as a reach target region of the capsule medical device (the predetermined capsule medical device described above) to be inserted into the body of the subject. Thereafter, the pretest capsule 31 is excreted from the body of the subject together with a bodily waste. In this case, the user can detect the pretest capsule 31 excreted from the body of the subject by the time when a predetermined time has elapsed since the subject orally ingests the pretest capsule 31. Based on this fact, the user determines that there is no problem in the passability of the predetermined capsule medical device through the lumen of the subject (that is, the predetermined capsule medical device orally ingested by the subject can sequentially pass through the inside of the lumen and reach the desired examination target organ).

As described above, in the fourth embodiment, an expandable and shrinkable inner casing simulating an external diameter of a capsule medical device smaller than that of a predetermined capsule medical device is arranged within a expandable and shrinkable outer casing simulating the external diameter of the predetermined capsule medical device. The outer casing is first-shrink-deformed conforming to the external diameter of the inner casing at the first timing based on the operation of a shape manipulating unit in which plural desired times are set in advance. The outer casing is second-shrink-deformed together with the inner casing conforming to the external diameter of the shape manipulating unit at the second timing after the first timing, and other configurations are set similar to those of the first embodiment. Therefore, the outer casing can be shrink-deformed at multiple stages within the lumen of the subject, thereby causing the single outer casing to sequentially simulate external diameters of plural types of capsule medical devices. As a result, operational effects similar to those of the first embodiment can be achieved, and there can be provided a lumen passability checking device capable of checking a lumen passability of plural types of capsule medical devices having different external diameters, by having the subject orally ingested the pretest capsule at one time.

Fifth Embodiment

A fifth embodiment of the present invention is described next. In the first embodiment described above, a through hole is formed in the communication part 2b of the outer casing 2 at a desired timing set in advance, thereby shrink-deforming the outer casing 2. On the other hand, in the fifth embodiment, an opening part of an outer casing is closed by using a dissoluble unit that can be dissolved by a predetermined substance in the body of the subject. The outer casing is shrink-deformed at timing when the dissoluble unit is dissolved.

Figure 12:
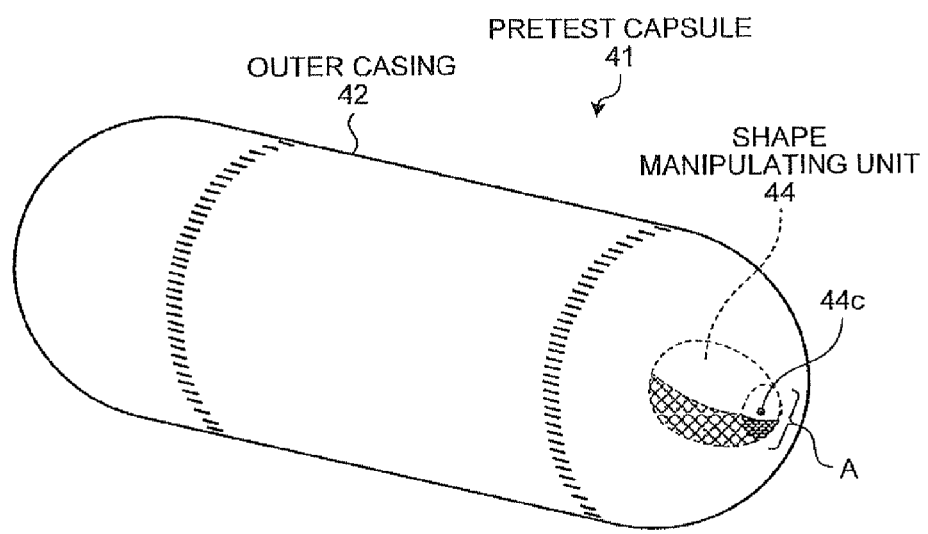
FIG. 12 is a schematic diagram for depicting a configuration example of a pretest capsule according to a fifth embodiment of the present invention.
Figure 13:
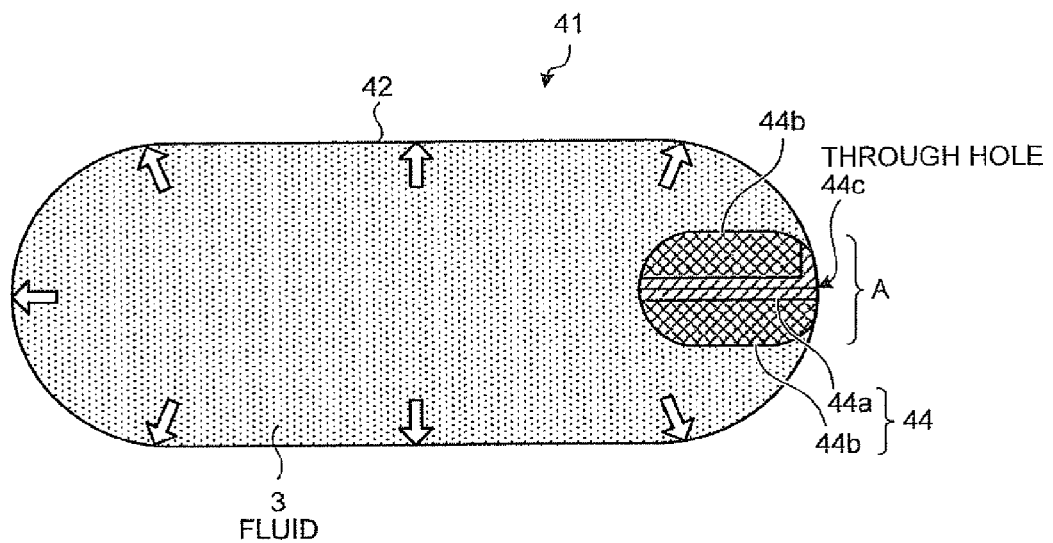
FIG. 13 is a schematic vertical cross-sectional view for exemplifying an internal configuration of the pretest capsule according to the fifth embodiment of the present invention.

FIG. 12 is a schematic diagram of a configuration example of a pretest capsule according to the fifth embodiment of the present invention. FIG. 13 is a schematic vertical cross-sectional view for exemplifying an internal configuration of the pretest capsule according to the fifth embodiment of the present invention. As shown in FIGS. 12 and 13r a pretest capsule 41 according to the fifth embodiment includes an outer casing 42 in place of the outer casing 2 of the pretest capsule 1 according to the first embodiment, and includes a shape manipulating unit 44 in place of the shape manipulating unit 4. Other configurations are the same as those of the first embodiment, and like constituent elements are denoted by like reference numerals.

The outer casing 42 is embodied by using an elastic member such as latex or silicon rubber, and contains the fluid 3. Similarly to the outer casing 2 of the pretest capsule 1 in the first embodiment, the expandable and shrinkable outer casing 42 is expanded by the pressure of the contained fluid 3, thereby forming a three-dimensional shape having an external diameter substantially equal to that of a desired capsule medical device (preferably, a capsule shape substantially similar to that of the capsule medical device). On the other hand, the outer casing 42 does not have the injection valve 2a and the communication part 2b (see FIG. 2), unlike the outer casing 2 in the first embodiment. The outer casing 42 lets in the fluid 3 from a through hole 44c of an elastic structure 44a of the shape manipulating unit 44 described later, instead of using the injection valve 2a, and flows out the fluid 3 from an opening part formed by dissolving a dissoluble unit 44b of the shape manipulating unit 44, instead of using the through hole formed in the communication part 2b.

Further, the outer casing 42 is connected to the shape manipulating unit 44 in a state of substantially containing the shape manipulating unit 44 near an opening part of the outer casing 42. The outer casing 42 is integrated with the shape manipulating unit 44 by covering the shape manipulating unit 44 in a state of exposing a part region A of the shape manipulating unit 44 from the opening part of the outer casing 42. The outer casing 42 maintains a three-dimensional shape having an external diameter substantially equal to that of a desired capsule medical device (preferably, a capsule shape substantially similar to that of the capsule medical device), while maintaining a state of being integrated with the shape manipulating unit 44. The opening part of the outer casing 42 is closed by the dissoluble unit 44b (described later) of the shape manipulating unit 44, and the blocked state of the opening part is released by the dissolution of the dissoluble unit 44b. When the blocked state of the opening part is released in this way, the outer casing 42 is continuously shrunk by flowing out the fluid 3, while maintaining the state of being integrated with the shape manipulating unit 44, and is finally shrink-deformed conforming to an external diameter of the elastic structure 44a (described later) of the shape manipulating unit 44.

The shape manipulating unit 44 manipulates a three-dimensional shape of the outer casing 42, and is formed by the elastic structure 44a that defines an external diameter of the outer casing 42 after shrink deformation, and the dissoluble unit 44b that closes the opening part of the outer casing 42. Specifically, the shape manipulating unit 44 is covered by the outer casing 42 in a state of exposing the part region A of the shape manipulating unit 44 (that is, each front end of the elastic structure 44a and the dissoluble unit 44b), and is also fixedly arranged near the opening part of the outer casing 42. In an initial state, the shape manipulating unit 44 closes the opening part of the outer casing 42, and dissolves the dissoluble unit 44b, thereby releasing the closed state of the opening part of the outer casing 42. The shape manipulating unit 44 releases the closed state of the opening part of the outer casing 42 in this way to communicate the inside and outside of the outer casing, to flow out the fluid 3 from the outer casing 42. With this arrangement, the shape manipulating unit 44 decreases the pressure of the fluid 3, thereby shrink-deforming the outer casing 42.

The elastic structure 44a is an elastic member having the through hole 44c through which an injection needle for injecting the fluid 3 into the outer casing 42 is inserted. The elastic structure 44a is fixed near the opening part of the outer casing 42 in a state of closing a part of the opening part of the outer casing 42 from the inside. In this case, the elastic structure 44a has one end of the through hole 44c arranged within the outer casing 42, and has the other end of the through hole 44c arranged at the outside of the outer casing 42. The through hole 44c is in a closed state, which is openable and closable by an elastic force of the elastic structure 44a, and permits the fluid 3 to flow through the through hole 44c via a duct member such as an injection needle only when the duct member is inserted into the through hole 44c.

Further, the elastic structure 44a is a structure having an external diameter at least smaller than that of the capsule medical device, and can easily pass through a passage barrier of the capsule medical device such as a stenosis part existing within the lumen of the subject. The elastic structure is covered by the outer casing 42 in a state of being in substantially close contact with an internal surface of the outer casing 42, thereby defining an ultimate external diameter of the outer casing 42 after shrink deformation. In this case, the outer casing 42 is in a state of being shrink-deformed conforming to an external diameter of the elastic structure 44a. Consequently, the external diameter of the shrink-deformed outer casing 42 becomes substantially equal to the external diameter of the elastic structure 44a. A three-dimensional shape of the elastic structure 44a may be a capsule shape substantially identical to that of a desired capsule medical device.

The dissoluble unit 44b is formed by a substance that is dissolved by a predetermined substance in the body of the subject, and is arranged on an external surface of the elastic structure 44a. Specifically, the dissoluble unit 44b is dissolved by being in contact, for a predetermined time or more, with a specific substance in the body inside a reach target region of the desired capsule medical device to be orally ingested by the subject (that is, a desired examination target organ) or within the organ nearer to the oral cavity than to the examination target organ. For example, when the desired examination target organ is large intestine, the dissoluble unit 44b is formed by an enteric substance such as chitosan or gelatin that is dissolved by a substance existing within the large intestine or small intestine. When the desired examination target organ is the small intestine, the dissoluble unit 44b is formed by a substance that can be dissolved by an alkali substance such as bile or is formed by an enteric substance. When the desired examination target organ is stomach, the dissoluble unit 44b is formed by a substance that is dissolved by a substance existing within the stomach or within the oral cavity (such as stomach acid or saliva). The dissoluble unit 44b is fixed near the opening part of the outer casing 42 in a state of closing the opening part of the outer casing 42 from the inside together with the elastic structure 44a described above, and exposes a part of the dissoluble unit 44b from the opening part of the outer casing 42. The dissoluble unit 44b in a state of being exposed from the opening part is dissolved by being in contact with a predetermined substance in the body of the subject for a predetermined time or more, thereby releasing the closed state of the opening part of the outer casing 42.

Figure 14:
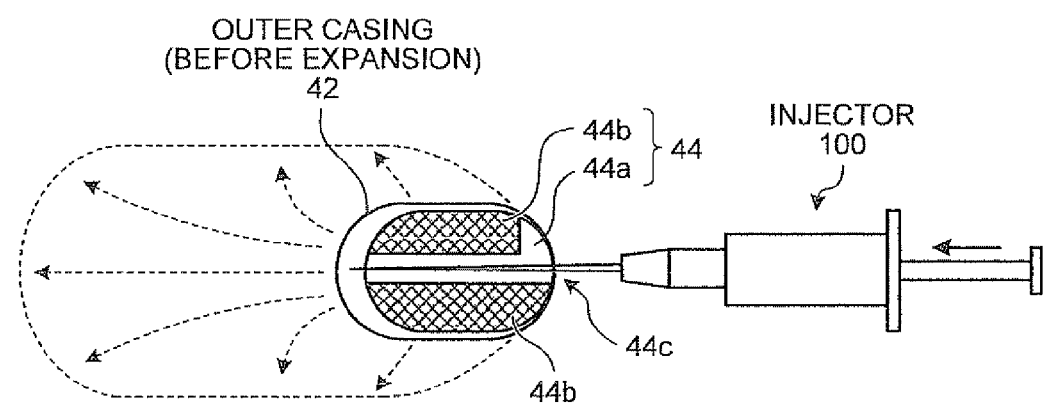
FIG. 14 is a schematic diagram for exemplifying a state of injecting a fluid into an outer casing.

A method of injecting the fluid 3 to expand the outer casing 42 (an example of a method of manufacturing a lumen passability checking device) is described next. FIG. 14 is a schematic diagram for exemplifying a state of injecting the fluid 3 into the outer casing 42. As shown in FIG. 14, in injecting the fluid 3 into the outer casing 42, an injection needle of an injector 100 is inserted through the through hole 44c of the shape manipulating unit 44, and the fluid 3 is injected into the outer casing 42 from the injector 100 via the pierced injection needle. By using the injector 100 in this way, the fluid 3 can be easily injected into the outer casing 42. As a result, the outer casing 42 is continuously expanded by the pressure of the fluid 3 injected by the injector 100, thereby ultimately forming an external diameter and a three-dimensional shape (a capsule shape) substantially equal to those of a desired capsule medical device. A device that injects the fluid 3 into the outer casing 42 is not limited to the injector 100, and can be a device such as a pump that can inject the fluid 3 via a duct member that can be inserted into the through hole 44c of the elastic structure 44a.

Figure 15:
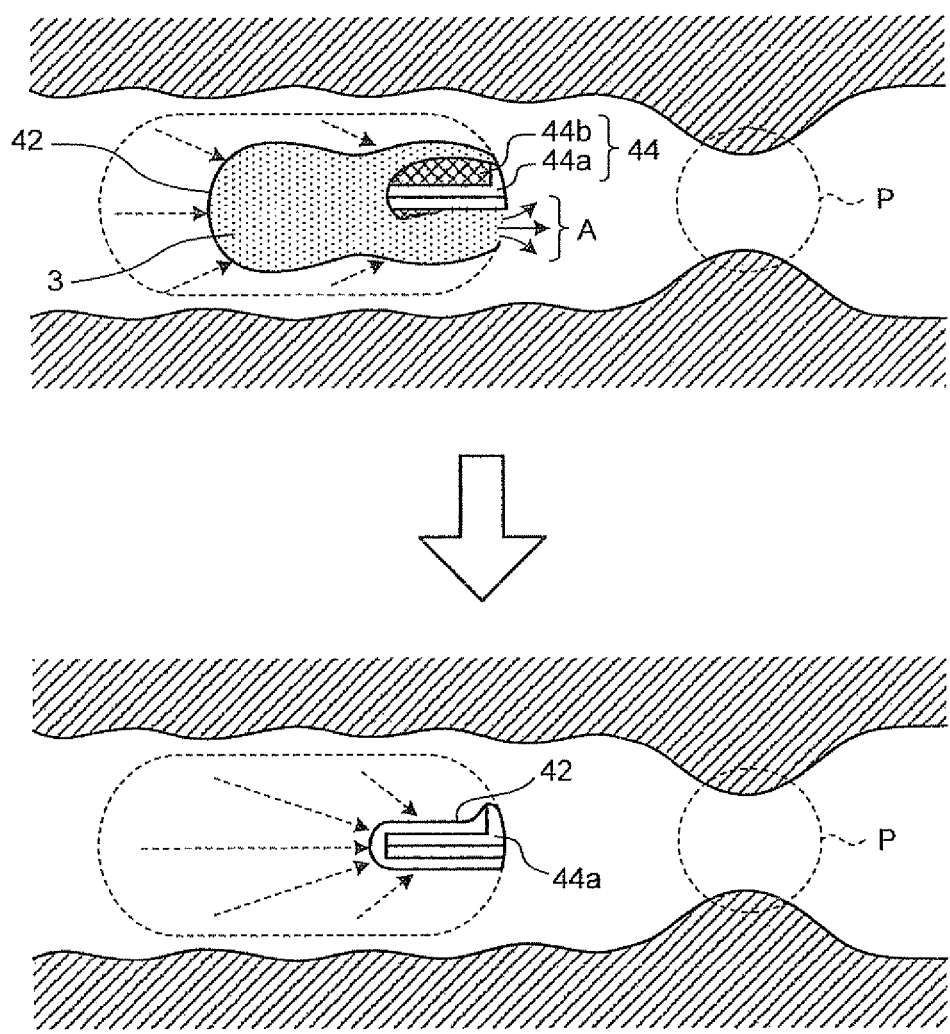
FIG. 15 is a schematic diagram for explaining shrink deformation of the outer casing of the pretest capsule according to the fifth embodiment of the present invention.

Shrink deformation of the outer casing 42 of the pretest capsule 41 according to the fifth embodiment of the present invention is described next in detail. FIG. 15 is a schematic diagram for explaining shrink deformation of the outer casing 42 of the pretest capsule 41 according to the fifth embodiment of the present invention. Before orally ingesting the capsule medical devices the subject orally ingests the pretest capsule 41 to check a passability of the capsule medical device through the lumen of the subject. Thereafter, the pretest capsule 41 advances within the lumen of the subject by a peristaltic movement or the like. When a passage barrier of the capsule medical device such as a stenosis part exists within the lumen of the subject, the pretest capsule 41 cannot pass through the passage barrier, and stagnates within the lumen as a result.

Specifically, as shown in FIG. 15, when the outer casing 42 is in the initial state (that is, when the outer casing 42 is in a state of forming a capsule shape having an external diameter substantially equal to that of the capsule medical device), the pretest capsule 41 is unable to pass through the stenosis part P, which is an example of the passage barrier of the capsule medical device, and stagnates there. In this case, the outer casing 42 of the pretest capsule 41 is shrink-deformed while flowing out the fluid 3 based on the operation of the shape manipulating unit 44. In this case, the outer casing 42 is continuously shrunk, while maintaining a state of substantially covering at least the elastic structure 44a of the shape manipulating unit 44 (that is, a state of being integrated with the shape manipulating unit 44). The outer casing 42 is finally shrink-deformed in a state of having an external diameter defined by the elastic structure 44a from the initial state of having the external diameter substantially equal to that of the capsule medical device.

The outer casing 42 shrink-deformed in this way, while maintaining a state of being integrated with the shape manipulating unit (ultimately, the elastic structure 44a) can form a three-dimensional shape having an external diameter substantially equal to that of the elastic structure 44a without scattering broken pieces or remainders of the outer casing 42 within the lumen. Thereafter, the shrink-deformed outer casing 42 and the elastic structure 44a (that is, the pretest capsule 41 after the shrink-deformation) can easily pass through the stenosis part P by a peristaltic movement or the like, and finally, it is naturally excreted from the body of the subject together with a bodily waste without leaving broken pieces or remainders of the outer casing 42.

The dissoluble unit 44b that closes the opening part of the outer casing 42 keeps in contact, for a predetermined time or more, with a substance in the body of the subject at the part region A as an exposure region of the shape manipulating unit 44. As a result, the dissoluble unit 44b is dissolved by the substance in the body at timing when a predetermined time has elapsed since the subject orally ingests the pretest capsule 41, and releases the closed state of the opening part of the outer casing 42. Thereafter, the dissoluble unit 44b dissolved by the substance in the body easily passes through the stenosis part P, and is easily excreted from the body of the subject. Consequently, after a passability of the capsule medical device through the lumen of the subject is checked, the dissoluble unit 44b hardly remains within the lumen of the subject, and does not interrupt various organ examinations to examine the inside of the organ of the subject by having the subject orally ingested the capsule medical device.

Preferably, the dissoluble unit 44b is in a colorless and transparent state when the dissoluble unit 44b is dissolved by a substance in the body of the subject, for the following reason. Even when a dissoluble substance of the dissoluble unit 44b remains within the lumen of the subject after checking the lumen passability of the capsule medial device, examinations within various organs to be performed by having the subject orally ingested the capsule medical device can be securely prevented from being interrupted due to the dissoluble substance.

When the subject orally ingests the pretest capsule 41 having the configuration described above, a user (an examiner) such as a doctor or nurse can check the passability of the capsule medical device through the lumen of the subject, similarly to the first embodiment.

As described above, in the fifth embodiment of the present invention, an opening part of an outer casing expanded by the pressure of a fluid is closed by a shape manipulating unit. A dissoluble unit of the shape manipulating unit maintaining the closed state of the opening part is kept in contact with a substance in the body of the subject for a predetermined time or more, thereby dissolving the dissoluble unit. Triggering the dissolution of the dissoluble unit, the closed state of the opening part of the outer casing is released. The outer casing is shrink-deformed by communicating the inside and outside of the outer casing, and other configurations are set similar to those of the first embodiment. Therefore, based on a simple configuration in which a dissolution of the dissoluble unit of the shape manipulating unit by a predetermined substance in the body triggers shrink deformation of the outer casing, the outer casing can be shrink-deformed, while maintaining a state of having the outer casing and the shape manipulating unit integrated together, similarly to the first embodiment. As a result, operational effects similar to those of the first embodiment can be achieved, and a lumen passability checking device capable of checking a passability of a capsule medical device through the lumen of the subject without scattering broken pieces or remainders of the outer casing within the lumen can be provided in a simple configuration.

Figure 16:
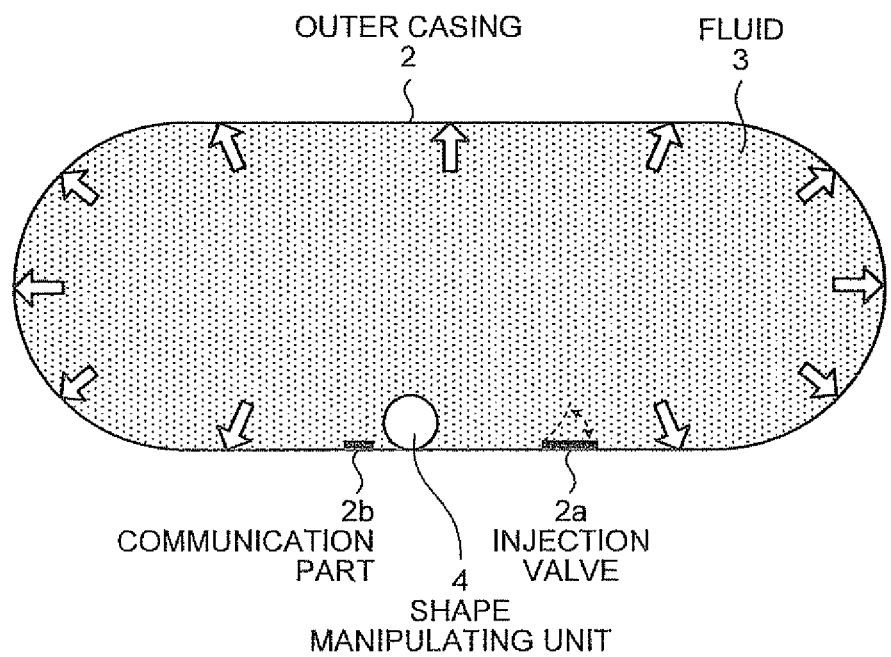
FIG. 16 is a schematic vertical cross-sectional view for depicting a configuration example of a pretest capsule with a shape manipulating unit having a spherical three-dimensional shape.

In the first to fourth embodiments of the present invention, a three-dimensional shape of a shape manipulating unit arranged within an outer casing has a capsule shape substantially identical to that of a capsule medical device. However, the shape is not limited thereto, and a three-dimensional shape of the shape manipulating unit can be a desired three-dimensional shape such as a sphere so long as the three-dimensional shape has an external diameter at least smaller than that of the capsule medical device. For example, the pretest capsule 1 according to the first embodiment can have an arrangement within the outer casing 2 a shape manipulating unit 4 having a spherical three-dimensional shape having an external diameter smaller than that of the capsule medical device, as shown in FIG. 16.

Figure 17:
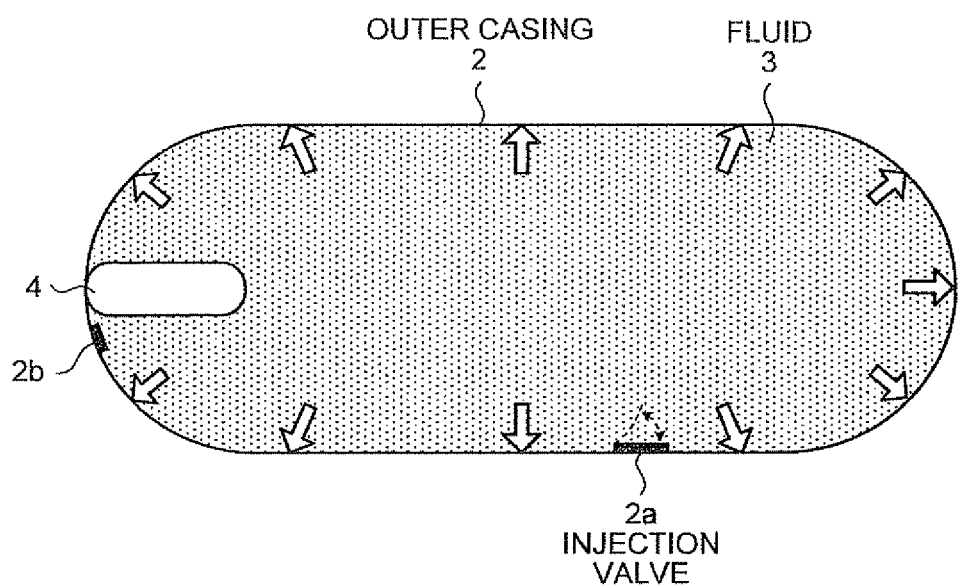
FIG. 17 is a schematic vertical cross-sectional view for depicting a configuration example of a pretest capsule having a shape manipulating unit arranged on an end forming a dome shape of an outer casing.

In the first to fourth embodiments of the present invention, a shape manipulating unit is fixedly arranged on the internal surface of a body forming a cylindrical shape of an outer casing or an inner casing forming a capsule shape. However, the arrangement is not limited thereto, and the shape manipulating unit can be fixedly arranged on the internal surface of an end forming a dome shape of the outer casing or the inner casing. For example, in the pretest capsule 1 according to the first embodiment, the shape manipulating unit 4 can be fixedly arranged on the internal surface of the end forming a dome shape of the outer casing 2, as shown in FIG. 17. In this case, the communication part 2b of the outer casing 2 can be provided near the shape manipulating unit 4.

Figure 18:
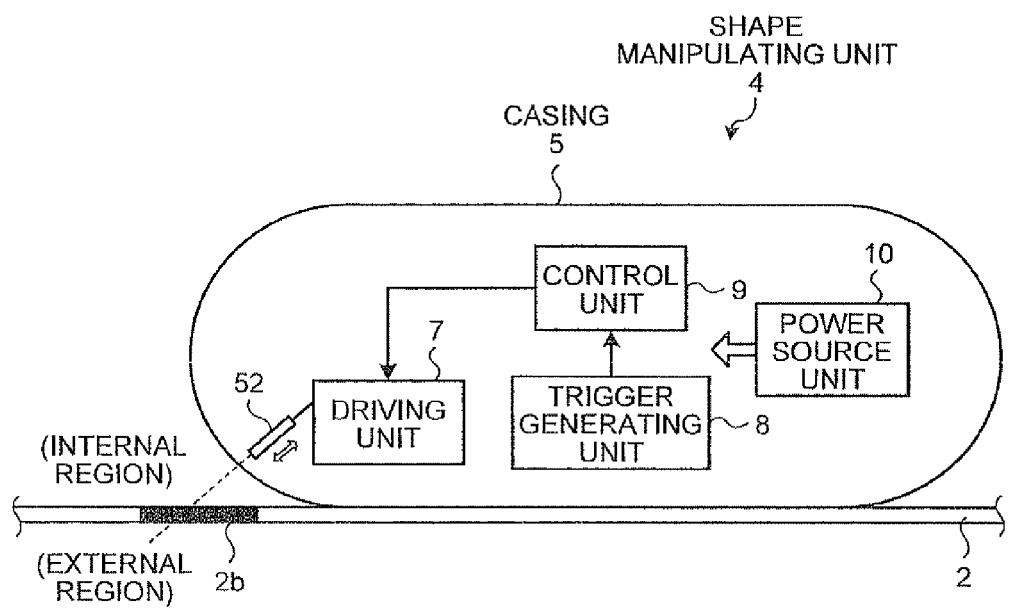
FIG. 18 is a block diagram for schematically depicting a configuration example of a shape manipulating unit that forms a though hole on an outer case by using a heat probe.

Further, in the first, second, and fourth embodiments of the present invention, a through hole that communicates the inside and outside of the outer casing is formed by using a needle. However, the configuration is not limited thereto, and a heat probe that forms a through hole in the communication part of the outer casing by heat treatment can be used in place of the needle. For example, in the pretest capsule 1 according to the first embodiment, as shown in FIG. 18, the pretest capsule 1 can have a heat probe 52 in place of the needle 6, the driving unit 7 can stretch the heat probe 52 into the communication part 2b of the outer casing 2, and a through hole can be formed in the communication part 2b by heat treatment of the heat probe 52. In this case, the driving unit 7 reciprocally moves the heat probe 52, and supplies heat energy to the heat probe 52.

Figure 19:
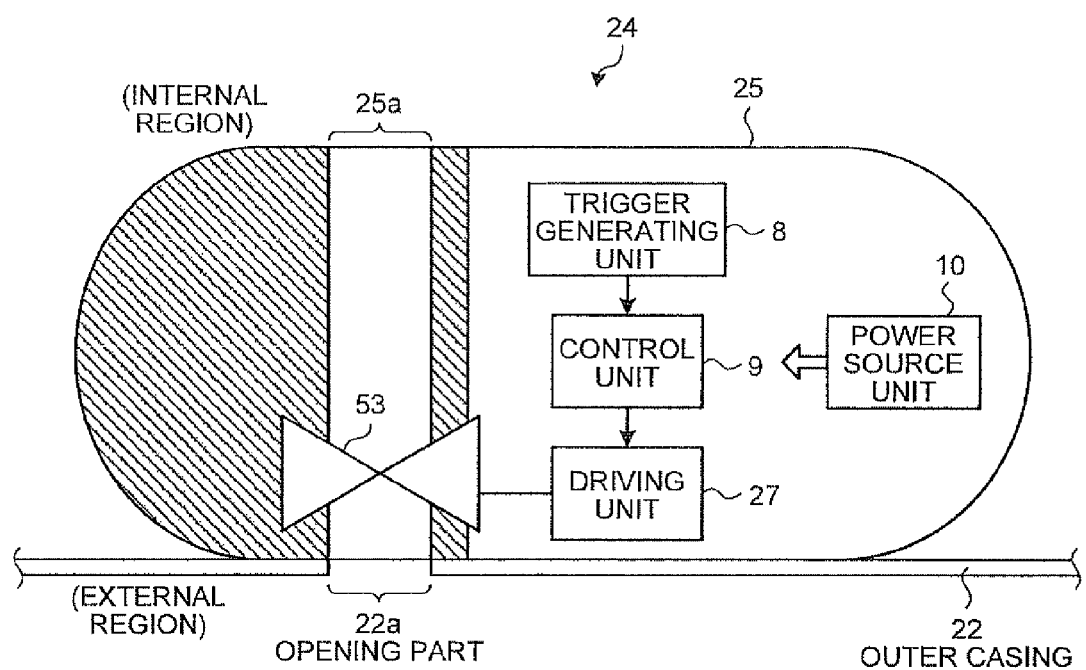
FIG. 19 is a block diagram for schematically depicting a configuration example of a first modification of a shape manipulating unit having a function of switching a communication duct that communicates inside and outside of an outer casing to be a communication state or a blocked state.

In the third embodiment of the present invention, the communication duct 25a that communicates the inside and outside of the outer casing is switched between the communication state and the blocked state by opening and closing the blocking member 26. However, the configuration is not limited thereto, and an openable and closable valve can be arranged in place of the blocking member 26, and the communication duct 25a can be switched between the communication state and the blocked state by the opening and closing of the valve. In this case, as shown in FIG. 19, for example, the shape manipulating unit 24 of the pretest capsule 21 according to the third embodiment can have a valve 53 in place of the blocking member 26, and the driving unit 27 can open and close the valve 53 to switch the communication duct 25a between the communication state and the blocked state.

Figure 20:
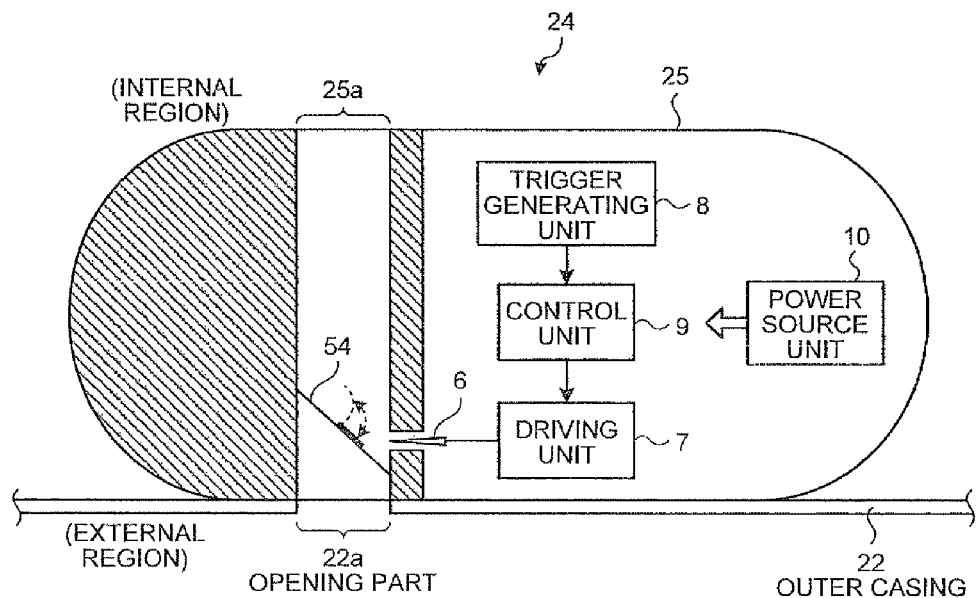
FIG. 20 is a block diagram for schematically depicting a configuration example of a second modification of the shape manipulating unit having a function of switching a communication duct that communicates inside and outside of an outer casing to be a communication state or a blocked state.
Figure 21:
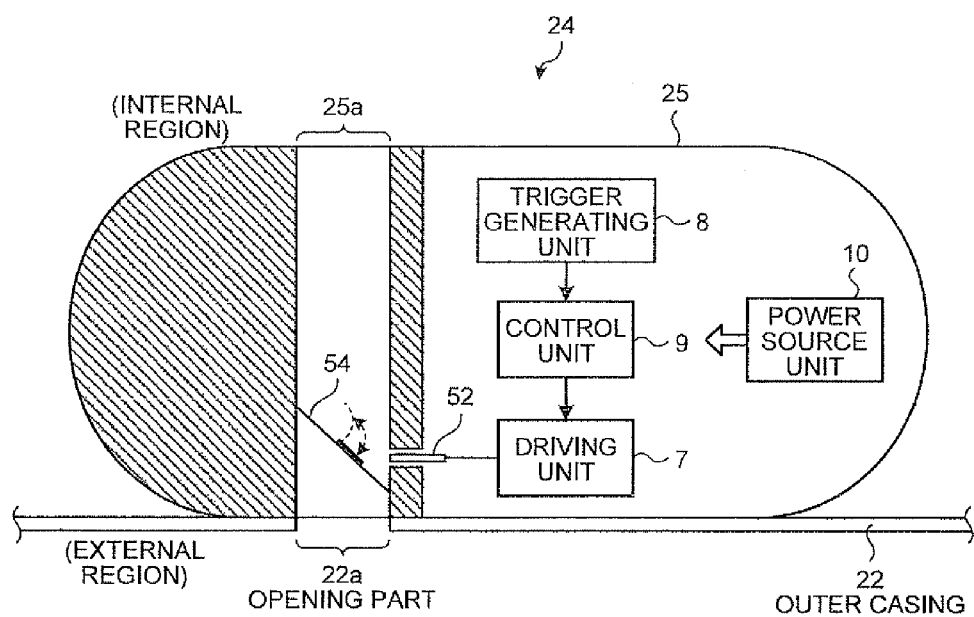
FIG. 21 is a block diagram for schematically depicting a configuration example of a third modification of the shape manipulating unit having a function of switching a communication duct that communicates inside and outside of an outer casing to be a communication state or a blocked state.

Further, in the third and fourth embodiments of the present invention, the communication duct 25a that communicates the inside and outside of the outer casing or the inner casing is switched between the communication state and the blocked state by opening and closing the blocking member 26 or the valve 36. However, the configuration is not limited thereto, and a blocking film can be arranged within the communication duct 25a, and the communication duct 25a can be switched to the communication state by forming a through hole on the blocking film by using a needle or a heat probe. For example, as shown in FIG. 20, the shape manipulating unit 24 of the pretest capsule 21 according to the third embodiment can have an arrangement of a blocking film 54 blocking the communication duct 25a within the communication duct 25a, and can have the needle 6 and the driving unit 7 that form a through hole on the blocking film 54, in place of the blocking member 26 and the driving unit 27. Alternatively, as shown in FIG. 21, the shape manipulating unit 24 of the pretest capsule 21 can have the heat probe 52 and the driving unit 7 that form a through hole on the blocking film 54 by heat treatment, in place of the blocking member 26 and the driving unit 27. The blocking film 54 may have a check-valve structure so that it permits an entrance of a fluid from an external region side (that is, the opening part 22a side) of the outer casing or the inner casing and inhibits flow of the fluid from an internal region side of the outer casing or the inner casing.

Figure 22:
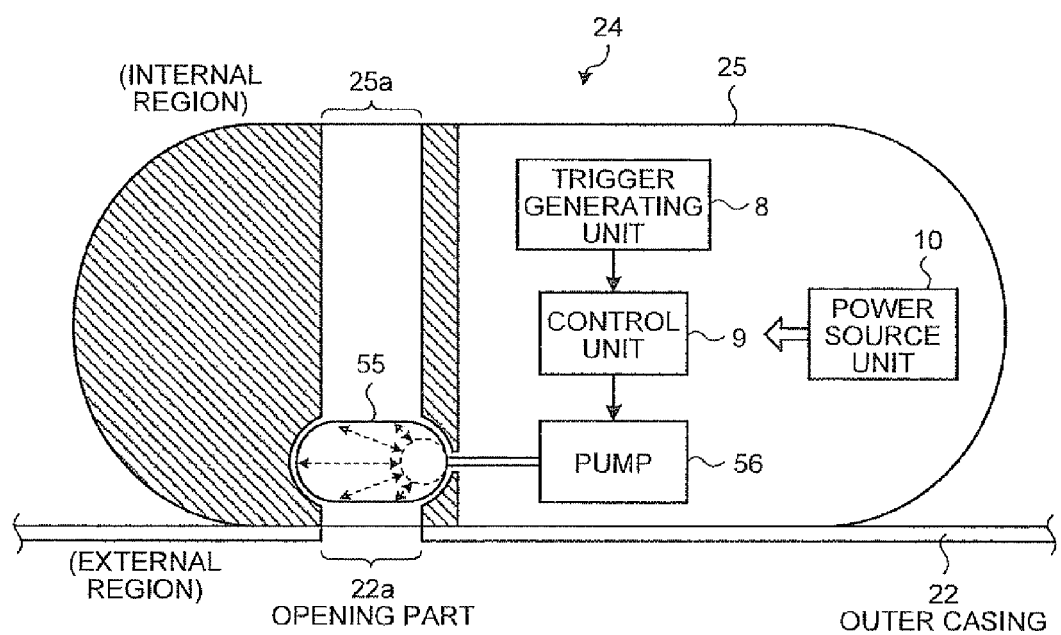
FIG. 22 is a block diagram for schematically depicting a configuration example of a fourth modification of the shape manipulating unit having a function of switching a communication duct that communicates inside and outside of an outer casing to be a communication state or a blocked state.

In the third and fourth embodiments of the present invention, the communication duct 25a that communicates the inside and outside of the outer casing or the inner casing is switched between the communication state and the blocked state by opening and closing the blocking member 26 or the valve 36. However, the configuration is not limited thereto, and an expandable and shrinkable elastic member can be arranged within the communication duct 25a, and the communication duct 25a can be set to the blocked state by expanding this elastic member, and the communication duct 25a can be set to the communication state by deflating the expanded elastic member. For example, as shown in FIG. 22, the shape manipulating unit 24 of the pretest capsule 21 according to the third embodiment can have an expandable and shrinkable elastic member 55 in place of the blocking member 26, and have a pump 56 in place of the driving unit 27. The pump 56 can set the communication duct 25a to the blocked state at a desired timing by expanding the elastic member 55 based on the control of the control unit 9. The communication duct 25a can be switched to the communication state at a desired timing by deflating the expanded elastic member.

Further, in the third and fourth embodiments of the present invention, the communication duct 25a that communicates the inside and outside of the outer casing or the inner casing is switched between the communication state and the blocked state by opening and closing the blocking member 26 or the valve 36. However, the configuration is not limited thereto, and a waterwheel or a propeller rotation device that is rotated to increase a flow rate of a fluid flowing within the communication duct 25a can be arranged, and a check valve that blocks the communication duct 25a by a spring force can be arranged at the opening part of the external region side of the communication duct 25a. In a suspended state of the rotation device, the check valve sets the communication duct 25a to a blocked state. When the rotation device rotates, a flow rate of the fluid within the communication duct 25a increases. In this state, the check valve can set the communication duct 25a to the communication state. For example, as shown in FIG. 23, the shape manipulating unit 24 of the pretest capsule 21 according to the third embodiment can have a rotation device 57 of a waterwheel shape or a propeller shape in place of the blocking member 26, and have a check valve 59 at the opening part of the external region side of the communication duct 25a. In this case, a driving unit 58 rotates the rotation device 57 based on the control of the control unit 9, thereby increasing the flow rate of the fluid flowing through the inside of the communication duct 25a at a desired timing. When the rotation device 57 is in a suspended state, the check valve 59 blocks the communication duct 25a by a predetermined spring force. On the other hand, when the flow rate of the fluid within the communication duct 25a is increased based on the rotation of the rotation device 57, the check valve 59 is opened outward of the communication duct 25a by the pressure of the fluid having the increased speed. As a result, the communication duct 25a is set to the communication state at a desired timing.

In the first, second, and fourth embodiments of the present invention, the injection valve 2a is formed to inject a fluid into the outer casing 2. However, the configuration is not limited thereto, and a through hole (an injection opening) can be formed on the outer casing 2 at the time of injecting the fluid into the outer casing 2. After the fluid is injected into the outer casing 2 via the through hole, the through hole can be closed by heat treatment or the like.

Further, in the first to fifth embodiments of the present invention, one shape manipulating unit is arranged within the outer casing. However, the configuration is not limited thereto, and plural shape manipulating units can be arranged within the outer casing. In this case, the plural shape manipulating units can be arranged at the inside of a body forming a cylindrical shape of the outer casing, or can be arranged at the inside of an end forming a dome shape. A desired number of these shape manipulating units can be fixedly arranged on the internal surface of the outer casing or the inner casing, or can be fixedly arranged on the external surface of the outer casing or the inner casing, so long as a state of integration with the outer casing is maintained. Similarly, a desired number of the injection valve 2a or a desired number of the communication part 2b can be arranged at desired positions of the outer casing 2. For example, plural injection valves 2a or plural communication parts 2b can be formed in the body forming a cylindrical shape of the outer casing 2, or one or more injection valves 2a or one or more communication parts 2a can be formed at an end forming a dome shape of the outer casing 2.

In the first to fifth embodiments of the present invention, a gas harmless to a human body (preferably, a colorless and transparent gas) is used as a fluid to expand the outer casing or the inner casing. However, the fluid is not limited thereto, and a desired liquid (an example of a fluid) can be injected into the outer casing or the inner casing, and the outer casing or the inner casing can be expanded by a pressure of the injected liquid. In this case, a liquid injected into the outer casing or the inner casing can be a liquid harmless to a human body such as a normal saline solution, or can be a drug for treating the subject, or can be a contrast agent, a stain, or a PET medical agent to check a position (for example, a position of a stenosis part) within the organ at which the outer casing is shrink-deformed. The liquid injected into the outer casing or the inner casing is preferably a colorless and transparent liquid similarly to the fluids 3 and 33 described above. From the viewpoint of maintaining an expanded state of the outer casing or the inner casing (that is, a state of forming an external diameter substantially equal to that of a desired capsule medical device), the fluid to be injected into the outer casing or the inner casing is preferably a gas capable of easily realizing a higher pressure.

Further, in the first to fourth embodiments of the present invention, an outer casing is shrink-deformed at timing when a predetermined time set in advance in a shape manipulating unit passes, using the passage of the predetermined time as a trigger. However, the configuration is not limited thereto, and the shape manipulating unit can include a pH detecting unit that detects a pH value within the lumen of the subject. The outer casing can be shrink-deformed at a desired timing triggered by the fact that a pH value detected by the pH detecting unit is equal to or higher (alkaline) or lower (acid) than a predetermined threshold value. Alternatively, the shape manipulating unit can include a receiving unit that receives a control signal transmitted from the outside, and the outer casing can be shrink-deformed at a desired timing triggered by the reception of the control signal at the receiving unit. Alternatively, the shape manipulating unit can include a detecting unit that detects a magnetic field, an electric field, or a wave applied from the outsider and the outer casing can be shrink-deformed at a desired timing triggered by the detection of the magnetic field, the electric field, or the wave from the outside at the detecting unit. The control signal can be transmitted to the receiving unit of the shape manipulating unit by radio communication, or can be transmitted to the receiving unit of the shape manipulating unit by human-body communication using a human body as a communication medium.

In the first to fifth embodiments of the present invention, a three-dimensional shape (a capsule shape) of a desired capsule medical device is simulated by an outer casing and an inner casing. However, the shape is not limited thereto, and a three-dimensional shape formed by the outer casing or the inner casing by the pressure of a fluid can be a desired three-dimensional shape other than a capsule shape, such as a spherical three-dimensional shape, or an oval shape forming an oval figure in a vertical cross-sectional view, as far as the three-dimensional shape has an external diameter substantially equal to that of the desired capsule medical device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A lumen passability checking device comprising:
    an expandable and shrinkable outer casing that contains a predetermined fluid, is expanded by a pressure of the contained fluid, and forms an external diameter equal to that of a capsule medical device to be inserted into a body of a subject; and
    a shape manipulating unit that flows out the fluid contained in the outer casing to shrink-deform the outer casing, the shape manipulating unit comprising:
        a structure connected to the outer casing in a state of being inserted into an opening part of the outer casing, and having an external diameter smaller than that of the capsule medical device, and
        a dissoluble unit arranged on an external surface of the structure and dissolved by a predetermined substance in the body of the subject,
    wherein:
        the structure is an elastic member arranged in the dissoluble unit and having a through hole through which the fluid is injected,
        the dissoluble unit closes the opening part of the outer casing, and releases closure of the opening part when the dissoluble unit is dissolved by the substance in the body,
        along with releasing of the closure of the opening part, the outer casing flows out the fluid via the opening part to be shrink-deformed, and
        the outer casing is shrink-deformed by flowing out the fluid, while maintaining a state of being integrated with the shape manipulating unit.

2. The lumen passability checking device according to claim 1, wherein the outer casing has a capsule shape the same as that of the capsule medical device.

3. The lumen passability checking device according to claim 1, wherein the fluid is a colorless and transparent liquid or gas.

4. A method of manufacturing a lumen passability checking device for checking a lumen passability of a capsule medical device to be inserted into a body of a subject, the method comprising:
    arranging at an opening part of an expandable and shrinkable outer casing, a dissoluble unit that can be dissolved by a substance in the body of the subject, in which a structure formed with an openable and closable through hole and having an external diameter smaller than that of the capsule medical device is arranged,
    closing the opening part of the outer casing,
    inserting a duct member into the through hole of the structure,
    injecting a fluid into the outer casing via the duct member,
    expanding the outer casing by a pressure of the fluid, and
    setting an external diameter of the outer casing to an external diameter equal to that of the capsule medical device.

5. The method of manufacturing a lumen passability checking device according to claim 4, wherein the structure is an elastic structure having the through hole that is closable by an elastic force.

* * * * *